US011622958B2

(12) United States Patent
Tietze et al.

(10) Patent No.: US 11,622,958 B2
(45) Date of Patent: Apr. 11, 2023

(54) BIFUNCTIONAL PRODRUGS

(71) Applicant: GEORG-AUGUST-UNIVERSITÄT GÖTTINGEN STIFTUNG ÖFFENTLICHEN RECHTS, Göttingen (DE)

(72) Inventors: Lutz F. Tietze, Goettingen (DE); Kamala Penchalaiah, Goettingen (DE)

(73) Assignee: GEORG-AUGUST-UNIVERSITÄT GÖTTINGEN STIFTUNG ÖFFENTLICHEN RECHTS, Göttingen (DE)

( * ) Notice: Subject to any disclaimer, the term of this patent is extended or adjusted under 35 U.S.C. 154(b) by 0 days.

(21) Appl. No.: 15/771,430

(22) PCT Filed: Oct. 28, 2016

(86) PCT No.: PCT/EP2016/076063
§ 371 (c)(1),
(2) Date: Apr. 27, 2018

(87) PCT Pub. No.: WO2017/072295
PCT Pub. Date: May 4, 2017

(65) Prior Publication Data
US 2018/0311212 A1  Nov. 1, 2018

(30) Foreign Application Priority Data

Oct. 29, 2015  (DE) .................... 10 2015 118 490.7
Feb. 3, 2016  (DE) .................... 10 2016 101 875.9
Mar. 23, 2016  (DE) .................... 10 2016 105 449.6

(51) Int. Cl.
*A61K 31/403* (2006.01)
*A61P 35/00* (2006.01)
*A61K 31/404* (2006.01)
*A61K 47/68* (2017.01)
*C07H 17/02* (2006.01)
*C07D 209/60* (2006.01)
*A61K 39/395* (2006.01)

(52) U.S. Cl.
CPC ...... *A61K 31/403* (2013.01); *A61K 39/39558* (2013.01); *A61K 47/6803* (2017.08); *A61K 47/6889* (2017.08); *A61P 35/00* (2018.01); *C07D 209/60* (2013.01); *C07H 17/02* (2013.01)

(58) Field of Classification Search
CPC .. A61K 31/381; A61K 31/382; A61K 31/403; A61K 31/4365; A61K 31/4436; A61K 39/39558; A61K 47/6803; A61K 47/6889; A61K 31/404; A61P 13/02; A61P 35/00; A61P 1/00; A61P 25/08; A61P 3/06; A61P 3/00; A61P 1/04; A61P 27/06; A61P 9/10; A61P 1/12; A61P 25/00; A61P 25/04; A61P 25/20; A61P 29/00; A61P 3/10; A61P 41/00; A61P 43/00; A61P 5/50; A61P 9/00; A61P 9/02; A61P 9/04; A61P 9/06; C07D 209/60; C07D 333/36; C07D 333/66; C07D 333/78; C07D 495/04; C07H 17/02
USPC ........................................................ 514/400
See application file for complete search history.

(56) References Cited

U.S. PATENT DOCUMENTS

| 6,660,742 | B2 * | 12/2003 | Lee ........................ C07C 215/76 |
| | | | 514/254.09 |
| 7,833,528 | B2 * | 11/2010 | Griffiths ................... B82Y 5/00 |
| | | | 424/136.1 |
| 9,815,784 | B2 * | 11/2017 | Beusker ............... C07D 403/06 |
| 10,092,659 | B2 * | 10/2018 | Santin ................ A61K 39/3955 |
| 2003/0037373 | A1 * | 2/2003 | Frazier ..................... A47G 9/02 |
| | | | 5/482 |
| 2018/0228906 | A1 * | 8/2018 | Helin ................. A61K 47/6829 |
| 2018/0311212 | A1 * | 11/2018 | Tietze ................ A61K 47/6889 |

FOREIGN PATENT DOCUMENTS

| DE | 10 2009 051799 A1 | 5/2011 |
| WO | 2015/023355 A1 | 2/2015 |
| WO | 2015/110935 A1 | 7/2015 |

OTHER PUBLICATIONS

Lutz Tietze et al. (Photoactivatable Prodrugs of Highly Potent Duocarmycin Analogues for a Selective Cancer Therapy, vol. 19, Issue5, Jan. 28, 2013, pp. 1726-1731; First published: Dec. 7, 2012, https://doi.org/10.1002/chem.201202773).*
Tanja Wirth et al: "The Two Faces of Potent Antitumor Duocarmycin-Based Drugs: A Structural Dissection Reveals Disparate Motifs for DNA versus Aldehyde Dehydrogenase 1 Affinity", Angewandte Dhemie International Edition, vol. 52, No. 27, pp. 6921-6925, Jan. 7, 2013.
Lutz F. Tietze et al: "Photoactivatable Prodrugs of Highly Potent Duocarmycin Analogues for Selective Cancer Therapy", Chemistry—A European Journal., vol. 19, No. 5, pp. 1726-1731, Jul. 12, 2012.

* cited by examiner

*Primary Examiner* — Samira J Jean-Louis
(74) *Attorney, Agent, or Firm* — WCF IP

(57) ABSTRACT

A first aspect of the invention relates to novel compounds and more precisely to novel bifunctional prodrugs and drugs. An additional aspect of the invention relates to antibody compound conjugates, wherein the compound is a claimed compound, and to pharmaceutical compositions containing the compound or antibody compound conjugate. The invention lastly relates to the use of this compound or antibody compound conjugates according to the invention in order to treat tumour diseases, particularly in mammals.

6 Claims, 14 Drawing Sheets

Examples of alkylating agents.

Examples of the active ingredient classes of the antimetabolites (4) and the mitotic inhibitors (6 and 7)

Representatives of the active ingredient classes of the topoisomerase inhibitors (8) and the cytostatic antibiotics (9 and 10).

Immunotherapies of malign tumors. A: immunocytokines, B: antibody-mediated tumor cytolysis C: activation of cytotoxic lymphocytes (CTL) by dendritic cells, D: enzyme-mediated conversion of prodrugs into drugs (ADEPT)), E: immunotoxin, F: antibody-radioisotope conjugate.

BIFUNCTIONAL PRODRUGS

In a first aspect, the present invention is directed to new compounds, more specifically to new bifunctional prodrugs and drugs. In a further aspect, the present invention is directed to antibody-compound conjugates, where the compound is a compound of the invention, and also to pharmaceutical compositions comprising the compound and/or the antibody-compound conjugate. Described, finally, is the use of this compound and/or of the antibody-compound conjugates according to the present invention for treating tumoral diseases especially in mammals.

PRIOR ART

The diverse manifestations of the cancerous condition necessitate individual therapeutic designs. As a response to the complexity of a tumoral disease, the majority of treatment methods presently in clinical use represent combinations of different therapeutic approaches. On the one hand, for readily accessible and clearly delimited tumors, surgical removal of the neoplastic tissue is employed as the method of choice. If, however, the tumor is harder to access, or if vital structures are involved, then radiation treatment is the method of choice. At a more advanced stage, where metastases have already formed or there is at least a risk of metastasis, chemotherapy usually takes place immediately. In tumor therapy, furthermore, the methods of hormone therapy, of immunotherapy, and therapy with angiogenesis inhibitors and kinase inhibitors are used.

In a case where metastasis has already been verified or is thought likely, and also in the case of systemic tumors, chemotherapy is currently the most important treatment method, despite often entailing severe side effects, such as disruption to blood count, immunodeficiency, mucositis, fever, nausea, vomiting, etc. The chemotherapeutic agents are customarily distributed via the blood stream to the whole body, and so are able to reach all the cells. Chemotherapeutic agents act cytostatically on human cells, meaning that they prevent cell multiplication, or they act cytotoxically, meaning that they bring about the death of the cells.

Given that the majority of cytostatic agents display their mechanism of action in proliferating cells, and since tumor cells are among the rapidly proliferating cell types, they are used as chemotherapeutic agents. However, the non-tumor cells of the person being treated are affected as well, particularly the cells of the bone marrow, the hair roots, or mucosal cells.

The cytostatic agents known presently and employed in chemotherapy are divided up according to their mechanisms of action into the classes of alkylating agents, antimetabolites, mitotic inhibitors, topoisomerase inhibitors, and cytostatic antibiotics.

The alkylating agents represent a numerically significant, structurally very diverse class of extremely reactive substances. Following optional prior activation of the drug, the active ingredient shows an electrophilic reaction, in particular with nucleic acids to form covalent bonds. This results in instances of DNA crosslinking, abnormal base pairings, or strand breakages, which prevent replication and lead ultimately to cell death. Typical examples of alkylating agents are cyclophosphamide or else cisplatin. A group of particularly effective alkylating agents includes, furthermore, the natural antibiotic CC-1065, the duocarmycins, yatakemycin, and also derivatives and analogs of this class of natural compounds.

In view of the necessity of chemotherapeutic treatments, the severe side effects of a large cohort of active ingredients used clinically, and the appearance of resistance toward many known chemotherapeutic agents, continual ongoing development is a necessity within the field of chemotherapeutic agents.

Chemotherapy of malignant disease is presently associated with severe side effects, since healthy tissue and malignant tissue are differentiated only by way of the heightened proliferation rate of cancer cells. New designs have therefore been developed which exploit genotypic and phenotypic properties of tumor cells and allow the targeted activation of reversible detoxified prodrug directly at the site of action. Targeted activation of this kind may be accomplished, for example, by an altered pH, such as a lowering in pH, for example. Another possibility is that referred to as ADEPT (Antibody-Directed Enzyme Prodrug Therapy). In this case, antibody-enzyme conjugates are utilized whose effect is to convert the nontoxic prodrug into the drug directly at the tumor, these conjugates achieving high selectivity. This binary therapeutic approach consists of two steps. First of all, a defined amount of an antibody-enzyme conjugate is administered, and is then distributed through the blood stream throughout the organism. The conjugate binds to specific antigens on tumor cell surfaces or is broken down and/or excreted by the body. When the unbound antibody-enzyme conjugate can no longer be detected, the prodrug is administered, in the second step. The prodrug, which as far as possible is not toxic, is likewise distributed in the entire organism and undergoes targeted toxification in the tumor tissue, by virtue of the enzyme which, ideally, is present only at the tumor surface, in the form of the antibody-enzyme conjugate. After penetration through the cell membrane, the drug released then develops its toxic effect, while the enzyme continues to be active on the outside of the tumor cell and is able to activate further prodrug molecules. In the context of this approach, cleavage of the prodrugs by endogenous enzyme systems ought as far as possible not to take place, since otherwise the activity of the therapy would be diminished or eliminated. Disadvantages of existing prodrugs, however, are insufficient difference in cytotoxicity between the prodrug and the drug generated from it, and also inadequate cytotoxicity of the resultant drug itself.

As a guideline in the development of compounds for the ADEPT design, the $QIC_{50}$ ($QIC_{50}=IC_{50}$ (prodrug)/$IC_{50}$ (prodrug in the presence of the enzyme)) ought to be greater than 1000 and the cytotoxicity of the parent drug ought to exhibit an $IC_{50}$ (toxin concentration at which cell growth is prohibited by 50%) of less than 10 nM.

Another approach to the targeted treatment of malignant tumors is that of prodrug monotherapy. This is based on the presence of enzymes which are overexpressed in tumors and which are capable of cleaving a corresponding prodrug to release the associated drug. One possible enzyme, for example, is β-D-glucuronidase, which has been verified at elevated concentrations in necrotic regions of tumoral tissues. Alternatively, conjugates formed from active ingredients and tumor-specific ligands may also be used for selective targeting in cancer therapy. Here, after selective binding of the ligand to a receptor on the tumor surface, the conjugate is internalized and, subsequently, intracellular release takes place.

Further processes in addition to the ADEPT process described above are the processes, known to the skilled person, of PDEPT (Polymer-Directed Enzyme Prodrug-Therapy) or MDEPT (Macromolecular-Directed Enzyme Prodrug Therapy) and also VDEPT (Virus-Directed Enzyme Prodrug Therapy) or GDEPT (Gene-Directed Enzyme Prodrug Therapy). The last two processes stated, in particular, represent possibilities for strengthening the prodrug monotherapy referred to above.

For the ADEPT design, clinical studies have already been carried out. It emerged that the ADEPT design per se is suitable for selective tumor therapy, but that there is still room for improvement in various respects in order to allow selective and efficient therapy. One of these key respects for improvement encompasses the provision of new and effective prodrugs which exhibit a high difference in cytotoxicity between the prodrug and the corresponding drug, high cytotoxicity of the drug, and a short plasma half-life for the drug.

There continues, therefore, to be a demand for provision of corresponding prodrugs which have a high cytotoxicity difference relative to the drug and which as prodrugs themselves display low cytotoxicity. The active ingredient (drug) formed itself is to have very high cytotoxicity.

For analogs of the antibiotic CC-1065 and of the duocarmycins, a variety of different experiments have been carried out to achieve the objective identified above. CC-1065 itself has an $IC_{50}$ of 20 pmol, but in animal experiments led to delayed lethal hepatotoxicity and is therefore not suitable for clinical applications. Attempts were therefore made to prepare corresponding analogs of this compound. Accordingly, the DNA binding structural unit was modified, but the pharmacophore itself was modified in a wide variety of forms. Furthermore, seco and prodrug compounds were synthesized, which in general have toxicities and selectivities similar to those of the spirocyclopropyl compounds, e.g., CC-1065 or duocarmycins. Thus CC-1065 analogs have been described which reversibly, through glycosidation of the detoxified anti-methyl-seco-CBI-DMAI-β-D-galactoside (+)-(1S,10R) compound, achieve an outstanding result in terms of the cytotoxicity and the quotient of the cytotoxicity of the prodrug and of the prodrug in the presence of the activated enzyme. $QIC_{50}$ values of more than 4500 have been achieved.

Bifunctional alkylating agents are those having two reactive centers. They possess the possibility of causing intra- or inter-strand crosslinking of DNA. With regard to inter-strand crosslinking, particularly effective damage to the cells is achieved, and hence cell death. These compounds have a high cytotoxicity. Bifunctional derivatives of, for example, pyrrolobenzodiazidepines are described in the literature.

The diverse manifestations of cancerous conditions mean that they always necessitate individual therapeutic designs, with the majority of methods employed clinically combining different approaches. Three columns of cancer treatment are "steel", "beam" and "chemotherapy". In the case of solid, readily accessible, and clearly delimited neoplasias, surgical removal ("steel") offers the best opportunities for cure and the least side effects. If the tumor is difficult to access, is affecting vital structures, or involves, for example, bone metastases, then radiation treatment ("beam"; e.g., radiotherapy with gamma radiation or radioactive isotopes) is indicated. At the advanced stage where metastases have already formed or there is at least a risk of metastasis, chemotherapy usually takes place immediately. Among the therapeutics to find their way in here are more recent approaches such as, for example, treatment with angiogenesis inhibitors and kinase inhibitors, and also immunotherapy and hormone therapy.

Chemotherapy

Conventional antineoplastic chemotherapy normally entails severe side effects. Primarily these are disruptions in hematopoiesis and also in the gastrointestinal track (nausea, vomiting), mucositis (inflammation of mucus membranes), alopecia (hair loss), fever, immunodeficiency, infertility, and teratogenicity, all representing a severe burden on cancer patients both physically and mentally. In a chemotherapy, drugs are administered which are distributed in the peripheral system via the blood stream and so are able to reach virtually all the cells. On human cells, chemotherapeutic agents act either cytostatically, meaning that they prevent cell growth, or cytotoxically, meaning that they bring about cell death. On the basis of their mechanisms of action, the majority of substances preferentially cause damage to fast-proliferating cells, which take up the active ingredients more rapidly as a result of increased metabolism. The cells in question, however, include not only a large cohort of the tumor cells, but also non-malignant cells such as bone marrow cells, hair root cells or mucosal cells. Since they are also adversely affected, the typical side effects identified above are commonly observed in connection with a chemotherapy.

In accordance with their points of attack in the cell cycle, the cytostatic agents presently employed in cancer therapy are divided into the classes of alkylating agents, antimetabolites, mitotic inhibitors, topoisomerase inhibitors, and cytostatic antibiotics. The activity of the alkylating agents, which in structural terms are a very diverse class, is primarily not specific to phases. In the body, the drugs are frequently first activated to give the carbocation, before they react with N-, O- or S-nucleophiles in proteins or, in particular, nucleic acids, and form covalent bonds. Consequences are crosslinks of the DNA strands, abnormal base pairings, or strand breakages, which hinder replication and therefore cell division and lead ultimately to cell death.

Important members of this class of substance are nitrogen mustards such as, for instance, cyclophosphamide (1), which is converted only through biotransformation in the body into the actual active ingredient 2 (toxification) and is therefore referred to as a prodrug (FIG. 1*a*).

Platinum complexes as well, with cisplatin (3) (FIG. 1*a*) as the best-known member, belong to the class of the alkylating agents and act above all through intra-strand or inter-strand crosslinking of the DNA. Other members of the class of particularly active alkylating agents, furthermore, are the natural antibiotic CC-1065, the duocarmycins, yatakemycins, and derivatives and analogs of this class of natural compounds.

Antimetabolites are structural analogs of endogenous metabolic building blocks, which as antagonists displace the actual metabolites. They act phase-specifically preferentially in the S-phase of the cell cycle and inhibit important enzymes or lead to the formation of functionally incompetent macromolecules. One prominent example is the folic acid antagonist methotrexate (4), which as a false substrate inhibits dihydrofolate reductase and so prevents the formation of tetrahydrofolic acid (FIG. 1*b*). This acid in turn is essential for functions including purine synthesis and hence for cell proliferation.

Mitotic inhibitors (also called spindle poisons) intervene in the mitosis phase of the cell cycle, by binding to the β-unit of the tubulin dimer and so blocking either the synthesis of the nuclear spindles (e.g., colchicine, *vinca* alkaloids such as vincristine (6) and vinblastine (7), (FIG. 1*b*), or their breakdown (taxol, epothilone). As a consequence of the disrupted spindle apparatus, nuclear division and cell division can no longer take place.

Another class of cytostatic agents consists of inhibitors of topoisomerases I and II. The function of topoisomerases is that, during DNA replication, of unwinding the twisted strands, interrupting them, and then closing them again. If these enzymes are inhibited, they are no longer able to dissociate from the DNA, causing strand breakages and ultimately bringing about cell death. Typical members of this class of substance are etoposide, irinotecan and derivatives of the alkaloid camptothecin (8) (FIG. 1c).

The cytostatic antibiotics include primarily the anthracyclines daunorubicin (9) and doxorubicin (10) (FIG. 1c) which are isolated from species of *Streptomyces* and which act preferably in the S-phase of the cell cycle. They are intercalated into the DNA and thereby disrupt DNA and RNA synthesis. Furthermore, they may induce strand breakages through radical formation and inhibition of topoisomerase II.

Clinical benefit in the treatment of cancer has been significantly increased through the use of chemotherapeutic agents, particularly in cases of neoplasias that are difficult to access surgically, or where metastases have formed. However, in addition to the sometimes severe acute side effects, which in some instances necessitate termination of the therapy, chemotherapy also often carries late complications. These include the induction of secondary tumors, instances of damage to bone marrow, pulmonary fibroses, or immune defects. Another problem is the development of resistance by tumors to individual cytostatic agents or classes thereof, occurring because of the natural selection of resistant cells during a treatment.

In spite of the severe secondary effects and resistances, chemotherapy has become established as an indispensable treatment method. For that very reason, however, there is also a need for continual ongoing development of existing therapeutic approaches and active ingredients, with increased selectivity and hence fewer side effects as a primary objective.

Immunotherapy

The fourth and most recent pillar in cancer treatment that has developed is that of immunotherapy. For this, for example, cytokines or antibodies are used which have immunomodulatory or direct antiproliferative properties. Taking on a supporting role in this development are the characteristic cell surfaces of the different types of cell.

Located on the extracellular side of every cell membrane is the glycocalyx, which consists of glycolipids, glycoproteins, and glycosaminoglycans and whose functions include those of cell recognition, communication, and signal reception. Certain constituents of the glycocalyx function here as antigens which—presented on the surface—are specific, for example, for cancer cells (specific antigens) or are overexpressed in tumor cells by comparison with healthy cells (tumor-associated antigens). It is these antigens that represent the central point of attack of an immunotherapy: monoclonal antibodies are able to bind selectively to the antigens, thus specifically marking the cancer cells and subsequently—themselves or as a conjugate—destroying the malignant degeneracy. These immunoglobulins, prepared for the first time in 1975 by Köhler and Milstein, are nowadays accessible on a standard basis by means of the hybridoma technology. Known representatives of antitumor-active antibodies are trastuzumab against HER2/neu-positive mammacarcinomas, and bevacizumab as an angiogenesis inhibitor. FIG. 2 shows a number of examples of the immunotherapy of malignant tumors. One possibility is that of coupling immunoglobulin with cytokines (e.g., interleukin-2, IL-2), with the resulting immunocytokine then triggering the endogenous immune defense at the tumor (A). Another possibility is to link antibodies with T-lymphocytes, so producing direct cytolysis of the tumor cell (B). The fusion of cancer cells with antigen-presenting cells is a further approach for mobilizing the endogenous immune defense for the purpose of destroying neoplasias. The resulting hybrids carry out increased expression of tumor-associated antigens on their surface, and so activate cytotoxic lymphocytes (CTL) which, stimulated by the tumor antigen-presenting hybrids, eliminate cancer cells having identical antigens. A comparable effect may also be achieved through the loading of dendritic cells (DC) with tumoral proteins, tumoral peptides or tumoral DNA (C).

Another form of therapy, which has likewise met great interest, uses antibody-drug conjugates (ADCs) (E). Exploiting the antibody specificity, it is possible in the ideal scenario for toxins to be guided in a targeted manner to the tumor without damaging healthy tissue. Gemtuzumab-ozogamicin (Mylotarg®, conjugate of antibody against CD-33 and a calicheamicin derivative) was the first active ingredient of this type with market approval (USA), although it was withdrawn in the fall of 2010 because of severe side effects such as myelosuppression. The two more recent products Adcetris and Kadcycla, with MMAE and DM1 as toxins, have been recently approved. Contrasting with the antibody-drug conjugates is the ADEPT design (Antibody-Directed Enzyme Prodrug Therapy). In that case antibody-enzyme conjugates are used which carry out selective conversion at the cancer cell of reversibly detoxified active ingredients (prodrugs) into cytotoxic drugs (D). Also in existence is radioimmunotherapy, which couples antibodies with radioactive isotopes ($^{131}$I, $^{90}$Y) (F). This approach is employed not only in tumor therapy but also in diagnosis, where among other things it allows metastases to be localized.

One key problem in the development of antibody-drug conjugates is the cytotoxicity of toxin used, which is frequently too low and the systemic toxicity of the conjugate. One approach pursued to a solution is to use relatively nontoxic prodrugs of the highly toxic duocarmycin that after having been taken release the toxin into the cell. The bases for the studies to the present inventors are "dimeric" duocarmycin analogs, developed by us, in which two CBI units are connected via a diamide bond to dicarboxylic acids. Compounds of this kind have an $IC_{50}$ of up to 150 fmol, and therefore constitute the cytotoxic compounds, as known. However, these compounds are not capable of attaching a monoclonal antibody, since they lack corresponding functionalities. Recently, numerous dimeric duocarmycins have been presented that can be bonded via a linker to a monoclonal antibody. These compounds, however, all have high systemic toxicity and are in no way superior to the known ADCs.

The use of antibody drug conjugates (ADCs) is an innovative approach to improving the therapy of cancer. Thus the general problem in the treatment of malignant tumors is that the chemotherapeutic agents available have only a relatively small therapeutic window and that therefore there are massive side effects. In order to reduce the dose-limiting toxicity, it is necessary to develop substances which possess selective disruption of the cancer cells by an improved discrimination between normal and malignant cells. Suitable in principle for this purpose are ADCs, in which, usually, a small, cytotoxic molecule is connected to a monoclonal antibody that binds to tumor-associated antigens. As a result it becomes possible, via so-called targeting, to introduce the toxin selectively into a cancer cell without attacking normal cells. For high activity and compatibility, however, there are certain preconditions that must be met. Hence the toxin is required to have a high $IC_{50}$ of <1 nmol, but the conjugate with the antibody is required to have only low toxicity. There are many cases in which this is not ensured.

The monoclonal antibody used ought not, moreover, to bind to the epithelium of normal cells. Further difficulties lie in the choice of the linker, which must on the one hand be sufficiently stable not to release the toxin in the serum, but must be sufficiently labile to be cleaved off in the cell following endocytosis of the conjugate. A further problem lies in the reduction in the cytotoxicity of the toxin used through introduction of functionalities which allow attachment to the monoclonal antibody. In one of the most promising ADCs of the first generation, with a doxorubicin as toxin and with a Lewis Y antibody, the problem can be comprehended very readily. In that case, then, the inadequate cytotoxicity of the doxorubicin, the inadequate stability of the linker, and the inadequate selectivity of the antibody were responsible for the failure of the compound in the clinical studies. In addition to the two approved compounds, Adcetris and Kadcyla, there are further substances, with calicheamicin, MMAE, DM1 and DM4 as toxins, within clinical trialing. Substances containing a duocarmycin or a related compound are not among them. The disclosure content of WO2015023355 includes conjugates with bifunctional duocarmycin analogs. Those compounds, however, exhibit only moderate activity; this is probably due to the high toxicity of the conjugate and to the comparatively low cytotoxicity of the toxin used, which has lost activity as a result of the derivatization that has taken place.

WO2007089149 discloses conjugates with monofunctional duocarmycin analogs. In comparison to the bifunctional analogs, these compounds have the disadvantage of the lower cytotoxicity.

DE 10 2009 051 799 A1 discloses compounds which represent bifunctional alkylating agents (duocarmycin analogs) particularly for use in selective tumor therapy. A feature of the compounds described therein is that, as dimers, they are more cytotoxic than the monomeric prodrugs or drugs. A disadvantage of these compounds is that they do not provide suitable connections to antibody-compound conjugates. Moreover, with the compounds described therein, the prodrugs are converted to drugs (only) by means of enzymatically cleavable groups.

WO 2015/110935 A1 describes a large number of bifunctional cytotoxic agents. These includes CPI prodrugs and CBI prodrugs.

It is an object of the present invention to provide new compounds suitable for producing conjugates with, for example, antibodies, so as to guide the compounds in the form of prodrugs to the corresponding therapeutic targets, such as the target cells for example. There continues to be a demand for drugs and prodrugs that are suitable for chemotherapeutic agents and which, in a goal-directed manner, convey these agents to the target regions—the target cells, for example.

DESCRIPTION OF THE INVENTION

Figure 1A:
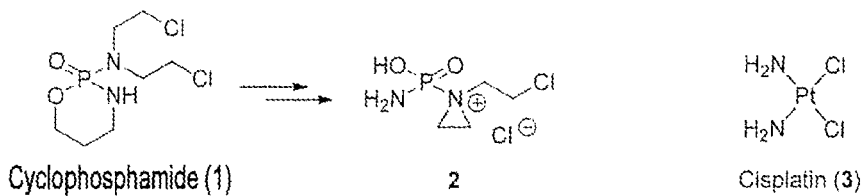
FIG. 1A. Examples of alkylating agents.
Figure 1B:
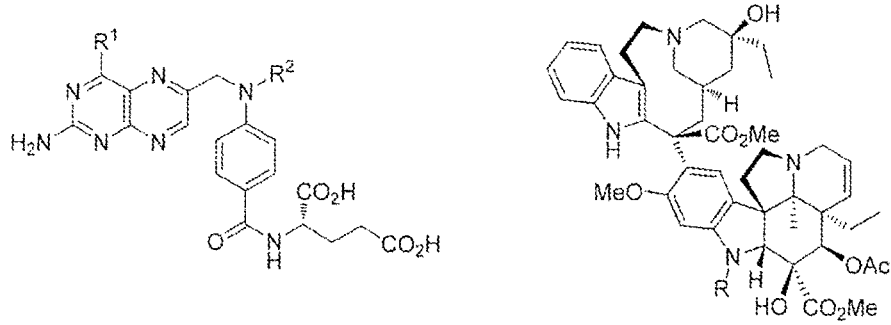
FIG. 1B. Examples of the active ingredient classes of the antimetabolites (4) and the mitotic inhibitors (6 and 7).
Figure 1C:
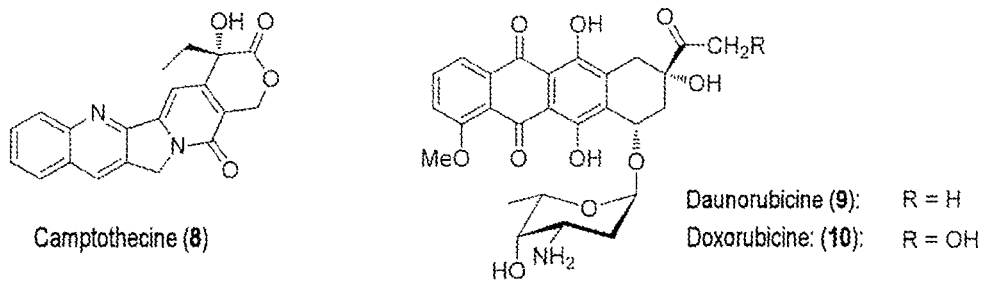
FIG. 1C. Representatives of the active ingredient classes of the topoisomerase inhibitors (8) and the cytostatic antibiotics (9 and 10).
Figure 2:
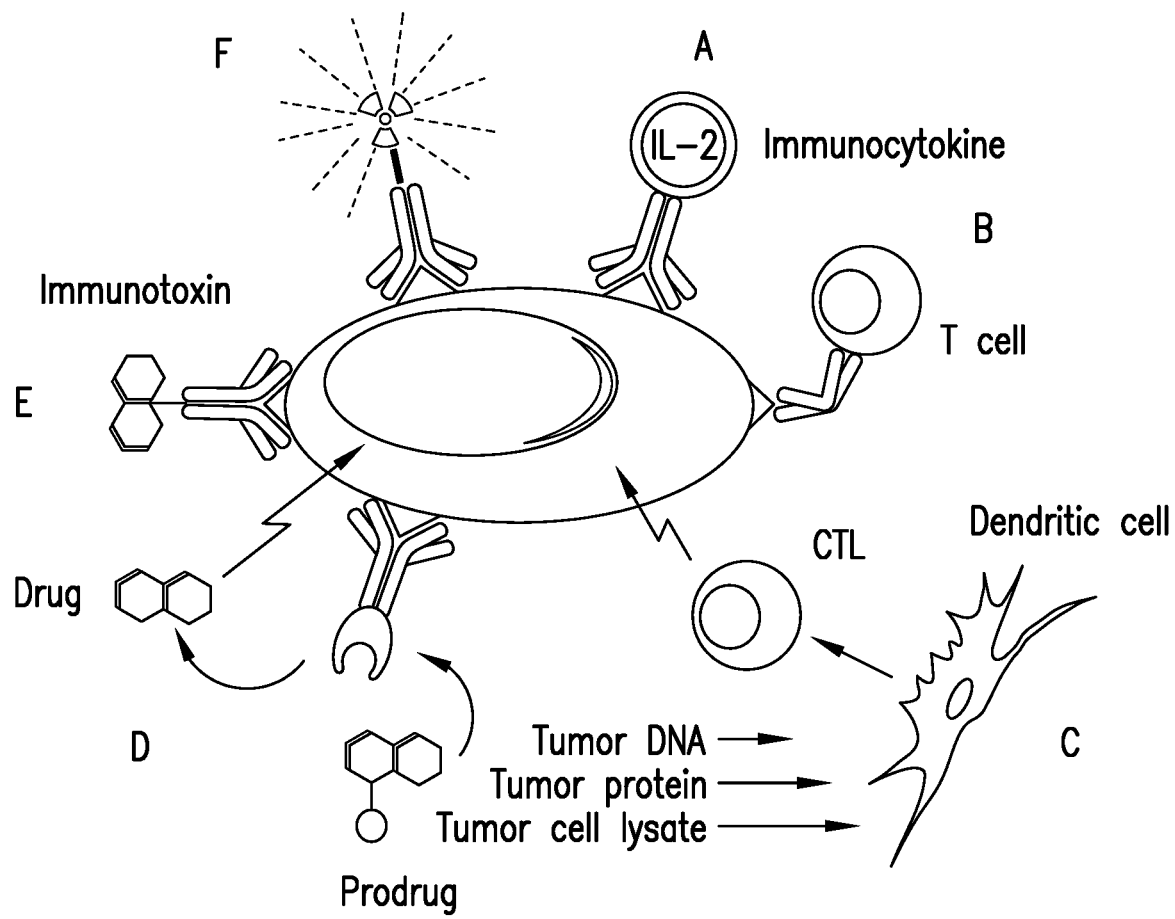
FIGS. 2A-F. Immunotherapies of malign tumors. (A) immunocytokines, (B) antibody-mediated tumor cytolysis, (C) activation of cytotoxic lymphocytes (CTL) by dendritic cells, (D) enzyme-mediated conversion of prodrugs into drugs (ADEPT), (E) immunotoxin, and (F) antibody-radioisotype conjugate.

Provided in accordance with the invention are new compounds which represent bifunctional alkylating agents especially for use in a selective tumor therapy. A feature of the new compounds described herein is that these new dimers are more cytotoxic than the monomeric prodrugs or drugs. The $IC_{50}$ of the compounds of the invention is typically in the pmol range. Furthermore, a much larger $QIC_{50}$ is achieved. This means that the quotient between the cytotoxicity of the drug and the cytotoxicity of the prodrug is substantially greater. As a result, it is possible to achieve better therapeutic efficacy in conjunction with lower prodrug cytotoxicity and hence to achieve fewer side effects on administration to the patients.

In a first aspect, compounds are provided of the general structure A-L-B, where A and B independently of one another are formed from the structure I

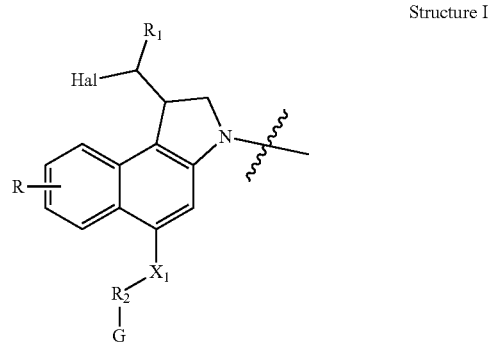

Structure I in which Hal is a halide selected from F, Cl, Br, I;
R is H or an optionally substituted $C_1$-$C_4$ alkyl group, an optionally substituted $C_1$-$C_4$ alkoxy group, an optionally substituted aryl group, an optionally substituted heteroaryl group, an optionally substituted $C_1$-$C_4$ alkylcarboxyl-$C_1$-$C_4$ alkyl group, Hal, CN, an optionally substituted $C_1$-$C_4$ alkylsulfanyl group, an optionally substituted arylsulfanyl group, a group $NR_z$ as defined below;

$R_1$ is H or a $C_1$-$C_4$ alkyl group or a $C_1$-$C_4$ alkoxy group;

$X_1$ is O, S, $NR_5$, where $R_5$ is selected from H and optionally substituted $C_1$-$C_4$ alkyl;

$R_2$ is selected from hydrogen or a cleavable substrate, more particularly a substrate which is cleavable by chemical reaction;

G independently at each occurrence is absent or is hydrogen or a functional group selected more particularly from an alkyne group, an amino group, a hydroxyl group, a thiol group, a carboxyl group, an azide group or a polyglycine group, where the functional group G is present at least once in the compound A-L-B;

L is a linker for the covalent linkage of A and B, where L has the structure Z—Y—Z';

where Z and Z' independently of one another are selected from C=O, OC=O, $SO_2$, $NR_z$, $NR_zC$=O, C=$ONR_z$, where each $R_Z$ independently of any other is selected from hydrogen and optionally substituted $C_1$-$C_4$ alkyl or optionally substituted $C_1$-$C_4$ acyl;

where Y is selected from a structure according to structure III or structure IV;

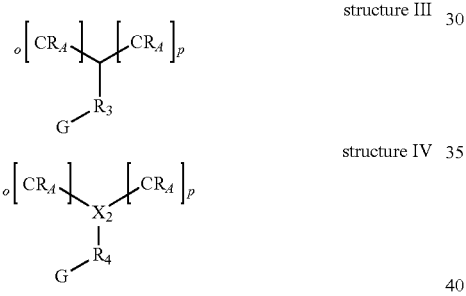

where each $R_A$ independently of any other is selected from hydrogen or optionally substituted $C_1$-$C_4$ alkyl or optionally substituted $C_1$-$C_4$ acyl;

o and p independently of one another are selected from an integer from 1 to 20; where o and p may adopt the same value or a different value;

G is as defined above;

$X_2$ is i) N or S or ii) an aryl or heteroaryl group, where $(CR_A)_o$ and $(CR_A)_p$ are located in meta position to this aryl group or to this heteroaryl group, $R_3$ is selected from $C_1$-$C_{10}$ alkyl, such as $C_1$-$C_4$ alkyl; $C_0$-$C_4$ alkylaryl $C_0$-$C_{10}$ alkyl group, such as $C_0$-$C_4$ alkylaryl $C_0$-$C_4$ alkyl group; $C_0$-$C_4$ alkylheteroaryl $C_0$-$C_{10}$ alkyl group, such as $C_0$-$C_4$ alkylheteroaryl $C_0$-$C_4$ alkyl group; or a cleavable substrate, more particularly a substrate cleavable by chemical reaction; or is not present;

$R_4$ is i) absent or is a $C_1$-$C_{10}$ alkyl group, such as a $C_1$-$C_4$ alkyl group; a $C_0$-$C_4$ alkylaryl $C_0$-$C_{10}$ alkyl group, such as a $C_0$-$C_4$ alkylaryl $C_0$-$C_4$ alkyl group; a $C_0$-$C_4$ alkylheteroaryl $C_0$-$C_{10}$ alkyl group, such as a $C_0$-$C_4$ alkylheteroaryl $C_0$-$C_4$ alkyl group; or a cleavable substrate, more particularly a substrate cleavable by chemical reaction, if $X_2$ is N or S, or ii) $R_4$ is a $C_1$-$C_{10}$ alkyl group, such as $C_1$-$C_4$ alkyl group; or a cleavable substrate, more particularly a substrate cleavable by chemical reaction; or is absent if $X_2$ is an aryl or heteroaryl group;

and pharmaceutically acceptable salts or pharmaceutically acceptable solvates thereof.

Employed presently are glycosidic prodrugs of dimeric duocarmycin that themselves have only a low toxicity, and whose activity following uptake into the cell is developed by elimination of the sugar component. The same applies to prodrugs wherein, through reaction with the phenolic hydroxyl group, the cytotoxicity is lowered, by means of a methyl group or a benzyl group, for example.

For the attachment of the toxins and their precursors (drugs and prodrugs) with monoclonal antibodies, in accordance with the invention, there are a number of possibilities.

A distinction is made generally between two fundamental approaches:
1. Use of noncleavable linkers. The assumption here is that, following uptake of the ADC into the cell and transport into the lysosome, there is complete breakdown of the antibody by means of proteinases and related enzymes. This leaves the toxin or its prodrug with a functional group to which the antibody was bonded.
2. Use of cleavable linkers, where cleavage can take place, for example, via acid-catalyzed hydrolysis, enzymatic transformation, or glutathione-induced cleavage of disulfides. Hence the pH in the lysosome is 4.8, whereas in the cytosol a pH=7.4 is found. Acid-labile linkers may contain hydrazone, acetal, enol ether, and azomethine functions. For an enzymatically cleavable linker, suitable compounds are those which contain sugar components or the dipeptide valine-citrulline, which can be cleaved by cathepsin B, which is strongly expressed intracellularly. The glutathione-mediated reductive cleavage of a disulfide linker is based on the finding that intracellularly, glutathione occurs at much higher concentrations than extracellularly.

The attachment of antibodies to the linker, in accordance with the invention, may be accomplished by the addition reaction of a lysine $NH_2$ group or a cysteine SH group with a maleimidocaproyl function, with a maleimido-methylcyclohexanecarboxylate function, with a maleimidodioxacaproyl function, or with comparable functionalities. Further attachments are possible via the linking of two amino functionalities with quadratic acid diethyl ester and comparable functionalities to form a diamide. The addition reaction of nucleophiles with α,β-unsaturated carbonyl compounds has also been employed. Another linking method is the 1,3-dipolar cycloaddition reaction of linkers having an alkyne or an azide group to antibodies which carry an azide or an alkyne group, respectively. Lastly, enzymatically induced linking of polyglycine substituted toxins and/or precursors thereof (prodrugs) to an antibody may take place by means of a sortase.

In one embodiment here, $R_2$, $R_3$ and/or $R_4$ is selected from a substrate which by enzymatic cleavage, such as by proteolytic, oxidative or reductive enzymes, plasmin, cathepsin, cathepsin B, beta-glucuronidase, galactosidase, mannosidase, glucosidase, neuramidase, saccharosidase, maltase, fructosidase, glycosylases, prostate-specific antigen (PSA), urokinase-type plasminogen activator (u-PA), metalloproteinase, cytochrome P450, or an enzyme which can be cleaved specifically by means of directed enzyme prodrug therapy, such as ADEPT, VDEPT, MDEPT, GDEPT, or PDEPT; or a substituent which can be transformed or cleaved off under hypoxic conditions or by reduction by nitroreductase, $R_2$, $R_3$ and/or $R_4$ being selected more particularly from a monosaccharide, disaccharide or oligosaccharide, more particularly hexoses, pentoses or heptoses, optionally as deoxy derivative or amino derivative and optionally substituted by halogen, $C_{1-8}$ alkyl, $C_{1-8}$ acyl, $C_{1-8}$ heteroalkyl, $C_{3-7}$ cycloalkyl, $C_{3-7}$ heterocycloalkyl, $C_{4-12}$ aryl or $C_{4-12}$ heteroaryl, amino groups or amide groups, or by amino, amido or carboxyl units which may optionally be substituted by halogen, $C_{1-8}$ alkyl, $C_{1-8}$ acyl, $C_{1-8}$ heteroalkyl, $C_{3-7}$ cycloalkyl, $C_{3-7}$ heterocycloalkyl, $C_{4-12}$ aryl or $C_{4-12}$ heteroaryl, amino radicals or amide radicals; dextran, dipeptide, tripeptide, tetrapeptide, oligopeptide, peptidomimetics, or combinations thereof; or a substrate which can be cleaved off by chemical reaction, where this substrate may comprise an acetal group, a benzyl group, or a substituted benzyl group.

The expression "functional group" refers presently to a substituent which is able, with a further structure, the target structure, more particularly proteins, especially antibodies or antibody fragments, to enter into bonding, preferably covalent bonding, in order to bind the compounds of the invention to these target structures, in particular in order to produce antibody-compound conjugates of the invention.

At the same time, after binding, these functional groups may also form a constituent of a cleavable substrate.

The expression "cleavable substrate" or "substrate which can be cleaved off" as presently used refers to a structure, such as the target structure, which under appropriate conditions and/or using appropriate molecules is split off from the prodrug and ultimately from the active drug. As observed, such cleavage may take place physically or chemically, more particularly enzymatically.

Target structures, in addition to the stated antibodies and antibody fragments, also include aptamers, lectins, biological response modifiers, enzymes, vitamins, growth factors, steroids, nutrients, sugar residues, oligosaccharide residues, hormones, and derivatives and combinations thereof.

The expression "antibody" refers presently to a naturally occurring or recombinant antibody or else antibody fragments; in one embodiment the antibodies are humanized antibodies or antibody fragments. The skilled person is aware of suitable antibodies and antibody fragments and their production. These antibodies or antibody fragments may have been modified in such a way that binding can take place to the compounds of the invention by way of the presently described functional group.

With the aid of the antibody-compound conjugates of the invention it is possible to guide the conjugates in a goal-directed manner to the target cells or target structures. In one embodiment the antibodies are directed at tumor-associated antigens or other cell surface constituents of the target structures, to allow target-driven introduction of the prodrugs into the cells.

The expression "antibody-compound conjugate" refers presently to a conjugate made up of antibody and compound of the invention. The compound in this case is, for example, a prodrug or drug molecule. Accordingly, it is also possible presently to refer to an antibody-prodrug conjugate or antibody-drug conjugate. This conjugate is one form of a target structure-compound conjugate, with, for example, the above-stated target structures and the compounds of the invention.

The linking of the compound of the invention to the antibody is accomplished via the functional group G, in order for the antibody of the invention, including antibody fragments, to be bonded covalently to the compound of the invention. This covalent bonding may optionally be parted again by means of suitable agents.

In a further embodiment of the present invention, the compound is one where o and p are identical or independently of one another are an integral uneven number from 1, 3, 5, 7, 9, 11, 13, 15, 17, and 19, Z and Z' are C=O, and each $R_4$ is, independently of any other, hydrogen or $CH_3$.

Furthermore, one embodiment relates to a compound where $R_2$ independently at each occurrence is a hydrogen or $CH_3$.

In accordance with the invention a compound is one where Hal is a Cl and $R_1$ is H.

One embodiment relates to a compound where L is a compound according to the structure II,

structure II where Y is defined as above.

Furthermore, one embodiment of the invention is one with a compound where $X_2$ is an aryl group, more particularly a benzyl group, Y is a structure IV where $R_4$ is a $C_1$-$C_4$ alkyl group, and G is a functional group presently defined.

Finally, one embodiment is a compound where the functional group G is presently only on the radical $R_2$.

In experiments in vitro, the compounds of the invention displayed excellent cytotoxicity values, with $IC_{50}$ values in the pmol range, in some cases below the pmol range. Furthermore, the compounds displayed an excellent quotient of the $IC_{50}$. The $QIC_{50}$ of the compounds tested was above 1000, with particularly suitable compounds showing values of more than 100 000.

This means that the compounds presently represented, which constitute new dimeric prodrugs and drugs of CC-1065 analogs, exhibit a very high cytotoxicity as a drug, whereas the prodrugs have only a relatively low cytotoxicity. As a result, these compounds ought to be significantly safer in therapeutic use. The compounds of the invention composed of dimers, furthermore, are substantially more cytotoxic than the monomeric prodrugs or drugs. The compounds are therefore distinguished by high activity in conjunction with fewer side effects in their application.

Earlier bifunctional CC-1065 analogs and duocarmycin analogs displayed only low selectivity, and the cytotoxicity values as well were similar to those of the monomeric analogs, and in some cases even lower.

A feature of the compounds of the invention is that they exhibit cytotoxicity values in the pmol range and have a very large quotient of the $IC_{50}$ values of the drug to the prodrug.

The expression "substituted" as used herein in relation in particular to alkyl, heteroalkyl, cycloalkyl, heterocycloalkyl, aryl, heteroaryl, and acyl refers to the fact that these groups one or more substituents selected from the group encompassing OH, =O, =S, =$NR^h$, =N—$OR^h$, $S^h$, $NH_2$, $NO_2$, NO, $N_3$, $CF_3$, ON, OCN, SCN, NCO, NCS, C(O)$NH_2$, C(O)H, C(O)OH, halogen, $R^h$, $SR^h$, S(O)$R^h$, S(O)$OR^h$, $S(O)_2R^h$, $S(O)_2OR^h$, OS(O)$R^h$, OS(O)$OR^h$, $OS(O)_2R^h$, $OS(O)_2OR^h$, OP(O)($OR^h$)($OR^i$), P(O)($OR^h$)($OR^i$), $OR^h$, $NHR^i$, N($R^h$)$R^i$, +N($R^h$)($R^i$)$R^i$, Si($R^h$)($R^i$)$R^j$, Si($R^h$)($R^i$)($R^j$), C(O)$R^h$, C(O)$OR^h$, C(O)N($R^i$)$R^h$, OC(O)$R^h$, OC(O)$OR^h$, OC(O)N($R^h$)$R^i$, N($R^i$)C(O)$R^h$, N($R^i$)C(O)$OR^h$, N($R^i$)C(O)N($R^j$)$R^h$, and the thiol derivatives of these substituents, or a protonated or deprotonated form of these substituents, where $R^h$, $R^i$, and $R^j$ independently of one another are selected from H and optionally substituted $C_{1-15}$ alkyl, $C_{1-15}$ heteroalkyl, $C_{3-15}$ cycloalkyl, $C_{3-15}$ heterocycloalkyl, $C_{4-15}$ aryl, or $C_{4-15}$ heteroaryl or a combination thereof; two or more of $R^h$, $R^i$, and $R^j$ are optionally joined to one another to form one or more carbon ring systems or heterocyclic ring systems.

The expression "alkyl" as used herein relates to straight-chain or branched, saturated or unsaturated hydrocarbonyl substituents; examples of the alkyl groups include a methyl, ethyl, propyl, butyl, pentyl, hexyl, octyl, decyl, isopropyl, sec-butyl, isobutyl, tert-butyl, isopentyl, vinyl, allyl, 1-butenyl, 2-butenyl, isobutenyl, pentenyl, and the like.

The expression "cycloalkyl" or "carbon ring systems" as used herein relates to saturated or unsaturated, nonaromatic hydrocarbon ring systems which may consist of one, two or more rings. Examples hereof include the following: cyclopropyl, cyclobutyl, cyclopentyl, cyclopentenyl, cyclopentadienyl, cyclohexyl, cyclohexonyl, etc.

The expression "heteroalkyl" as used herein relates to straight-chain or branched, saturated or unsaturated hydrocarbonyl substituents in which at least one carbon has been replaced by a heteroatom. The heteroatoms are preferably selected from S, N, O, and P.

The expression "aryl" as used herein relates to aromatic substituents which may consist of one or more rings fused with one another. Examples of aryl include the following: phenyl, naphthyl, and anthracenyl.

The expression "heteroaryl" as used herein relates to aromatic substituents which may consist of one or more rings fused with one another. In this case at least one carbon atom in the aromatic ring group has been replaced by a heteroatom. Examples of heteroaryl groups include the following: pyridyl, furanyl, pyrrolyl, triazolyl, pyrazolyl, imidazolyl, thiophenyl, indolyl, benzofuranyl, benzimidazolyl, indazolyl, benzotriazolyl, benzisoxazolyl, and quinolyl.

The expression "heterocycloalkyl" or "heterocyclic ring systems" as used herein relates to saturated or unsaturated, nonaromatic, cyclic hydrocarbonyl substituents which may consist of one or more rings fused with one another, where at least one carbon atom in one of the rings has been replaced by a heteroatom. Examples of heterocycloalkyls include the following: tetrahydrofuranyl, pyrrolidinyl, piperidyl, 1,4-dioxanyl, morpholinyl, piperazinyl, oxyzolidinyl, decahydroquinolyl.

The expression "acyl" as used herein relates to the functional group having the general structure $R_{AC}$—CH=O— where $R_{AC}$ represents an optionally substituted carbon radical, more particularly a hydrocarbon chain having $C_1$ to $C_8$ carbon atoms.

If expressions such as "optionally substituted" are used, these expressions refer to all of the following radicals, unless otherwise stated.

Therefore, the expression "optionally substituted alkyl, heteroalkyl, aryl, acyl" should be read as "optionally substituted alkyl, optionally substituted heteroalkyl, optionally substituted aryl, optionally substituted acyl".

Depending on the substituents, especially depending on the substituent $R_2$, $R_3$ and/or $R_4$ and the antibodies conjugated via G, the compounds can be introduced simply and in a directed way into cells. In one embodiment, $R_2$, $R_3$ and/or $R_4$ is preferably hydrogen.

In a further preferred embodiment, $R_2$, $R_3$ and/or $R_4$ represents a substrate which is cleavable, for example, enzymatically, in order to convert prodrugs featuring a cleavable product on the $R_2$, $R_3$ and/or $R_4$ substituent into drugs.

In one preferred embodiment, therefore, the $R_2$, $R_3$ and/or $R_4$ in the substrate comprises a cleavable product. Cleavage may be accomplished by chemical reaction, as for example on the basis of a change in the ambient conditions, such as pH, concentration of particular ions, etc.

In one preferred embodiment, $R_2$, $R_3$ and/or $R_4$ in the substrate comprises a cleavable substrate. This cleavable substrate is preferably one which by proteolytic enzymes, plasmin, cathepsin, cathepsin B, beta-glucuronidase, galactosidase, mannosidase, glucosidase, neuramidase, saccharosidase, maltase, fructosidase, glycosylases, prostate-specific antigen (PSA), urokinase-type plasminogen activator (u-PA), metalloproteinase, or an enzyme which can be cleaved specifically by means of directed enzyme prodrug therapy, such as ADEPT, VDEPT, MDEPT, GDEPT, or PDEPT; or a substituent which can be transformed or cleaved off under hypoxic conditions or by reduction by nitroreductase.

The radical $R_2$, $R_3$ and/or $R_4$ preferably comprises one selected from the group encompassing monosaccharide, disaccharide or oligosaccharide, more particularly hexoses, pentoses or heptoses, optionally as deoxy derivative or amino derivative, and optionally substituted by halogen, $C_{1-8}$ alkyl, $C_{1-8}$ acyl, $C_{1-8}$ heteroalkyl, $C_{3-7}$ cycloalkyl, $C_{3-7}$ heterocycloalkyl, $C_{4-12}$ aryl or $C_{4-12}$ heteroaryl, amino groups or amide groups, or by amino, amido or carboxyl units which may optionally be substituted by halogen, $C_{1-8}$ alkyl, $C_{1-8}$ acyl, $C_{1-8}$ heteroalkyl, $C_{3-7}$ cycloalkyl, $C_{3-7}$ heterocycloalkyl, $C_{4-12}$ aryl or $C_{4-12}$ heteroaryl, amino radicals or amide radicals; dextran, dipeptide, tripeptide, tetrapeptide, oligopeptide, peptidomimetics, or combinations thereof.

It is possible, furthermore, to utilize substituents which are labile under certain ambient conditions, such as hemiacetals and acetals, benzyl groups and substituted benzyl groups.

With the aid of the substrate $R_2$, $R_3$ and/or $R_4$, targeting of the compounds of the invention to target structures may be possible. In other words, goal-directed coupling of the compounds of the invention to target structures, for the targeting of these conjugates, for example, into the target cells or target tissue, is possible, and the corresponding introduction of these compounds of the invention into, for example, selected cells and cell types is possible. The compounds of the invention wherein $R_2$, $R_3$ and/or $R_4$ is a substrate other than H contain a cleavable or transformable group. The cleavage or the transformation of the compound of the invention with $R_2$, $R_3$ and/or $R_4$ other than H may be accomplished by chemical, photochemical, physical, biological or enzymatic processes under the corresponding conditions. These conditions include, for example, the provision of appropriate enzymes, the modification of the ambient medium, the action of, for example, radiation, such as UV light, etc. The skilled person is aware of corresponding methods. The substrate is correspondingly amenable to known methods such as ADEPT (Antibody Directed Enzyme Prodrug Therapy), PDEPT (Polymer-Directed Enzyme Prodrug Therapy) or MDEPT (Macromolecular-Directed Enzyme Prodrug Therapy), VDEPT (Virus-Directed Enzyme Prodrug Therapy) or GDEPT (Gene-Directed Enzyme Prodrug Therapy).

Correspondingly, a further aspect of the present invention is directed to an antibody-compound conjugate where an antibody is linked via the functional group G to the above-defined compound of the invention.

In one embodiment of this antibody-compound conjugate, the conjugate is one where the antibody is directed against a tumor antigen or an antigen which is expressed onto a target structure, such as a cell.

In a further embodiment, the antibody-compound conjugate is one where the antibody is one of an antibody, an antibody fragment, such as F(ab')$_2$, F(ab'), Fab, Fv, sFv, scFv.

The present patent application is directed, furthermore, to pharmaceutical compositions which comprise the compounds of the invention, optionally with pharmaceutically acceptable excipients or diluents. The compounds of the invention may in this case be present in the form of pharmaceutically acceptable salts or solvates. This means that the pharmaceutical composition comprises a compound of the invention or an antibody-compound conjugate of the invention.

Pharmaceutically acceptable salts are, in particular, acid addition salts which are formed correspondingly on amine groups. Equally possible are base addition salts or corresponding zwitter addition salts.

The expression "pharmaceutically acceptable solvates" refers to the association of one or more solvent molecules and a compound of the invention.

Examples of those solvent molecules which form pharmaceutically acceptable solvates are the following: water, isopropyl alcohol, ethanol, methanol, DSMO, ethyl acetate, and acetic acid.

The compounds of the invention are suitable particularly for producing pharmaceutical compositions suitable in tumor therapy. The monomers of the bifunctional compounds of the invention are known to be cytotoxic compounds suitable for tumor therapy. The present invention includes pharmaceutical compositions which in addition to the customary excipients or diluents comprise the compounds of the invention. The pharmaceutical preparations referred to above are conventionally produced by known methods, as for example by mixing the active ingredient or ingredients or excipient or excipients.

In general the compounds of the invention can be administered in total amounts of 0.5 to about 500, preferably 1 to 150 mg/kg body weight per 24 hours, optionally in the form of a plurality of individual doses, in order to obtain the desired outcomes. The skilled person is well aware of the possibilities for determining the dosage. It may be done as a function of the age, the body weight, the nature and severity of the disease in the patient, the type of preparation and administration of the medicinal product, and also the period or the interval of administration.

The seco-duocarmycin derivatives presently described carry, for example, alkyne, carboxyl, amino, azide, thiol, and hydroxyl groups, i.e., functional groups G which can be linked to antibodies very easily by means of the techniques discussed above.

Figure 5:
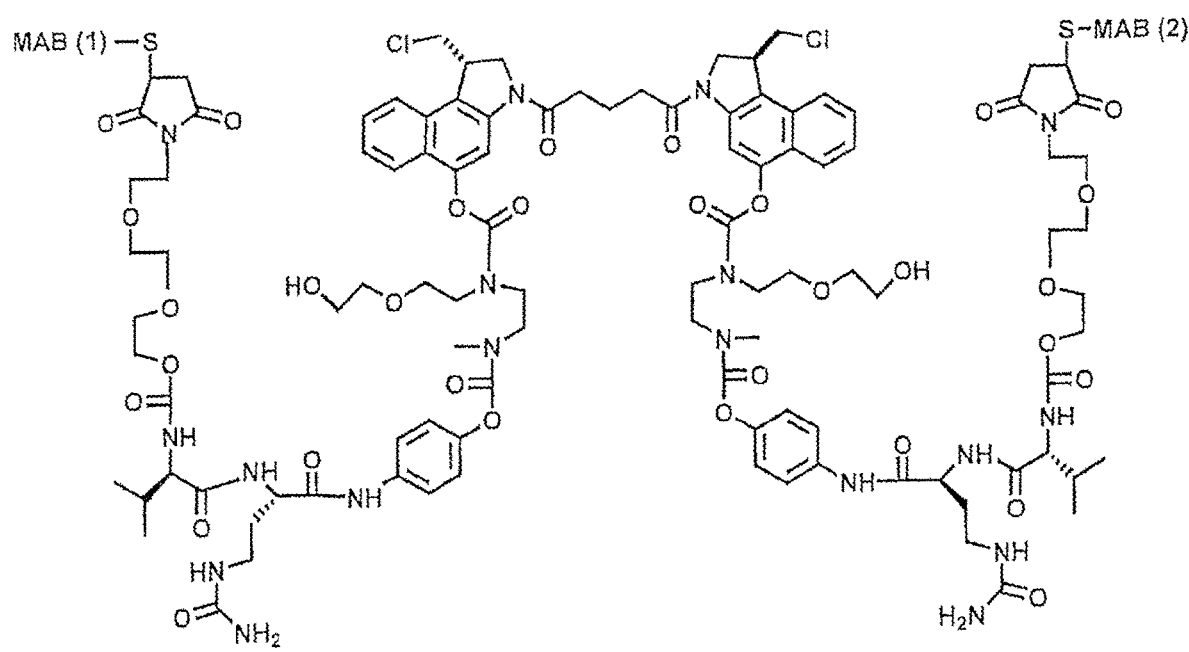
FIG. 5. Structure of an antibody-compound conjugate.

One out of many possible typical procedures for attaching an antibody to the bifunctional seco-duocarmycin analogs is shown in FIG. 5. The process represented even includes the possibility of inserting two different antibodies and in this way being able to address different tumor-associated antigens.

The use of duocarmycin analogs for the production of ADCs has the great advantage of their high cytotoxicity; in the case of the monofunctional derivatives, the latter is approximately IC$_{50}$=10 pM, whereas in the case of the bifunctional compounds it is even possible to achieve IC$_{50}$ values=150 fM. Furthermore, the compounds can be detoxified very efficiently by glycosidation, with figures of around 6000 in the case of the monofunctional and around 1 000 000 in the case of the bifunctional compounds. With other toxins, an approach of this kind is possible only with great difficulty. There are a number of pathways which can be taken for the formation of the ADCs:

1. In the case of the bifunctional duocarmycin analogs, there are three pathways that can be traveled
   a) insertion on the chain of a functionality which links the two CPI units to one another. In this case, however, there is a certain reduction in the cytotoxicity. Thus the compound 1 has a slightly increased IC$_{50}$ of 60 pM. For attachment via a cleavable linker of known type, it is possible to use functionalized benzene-1,3-diacetates.

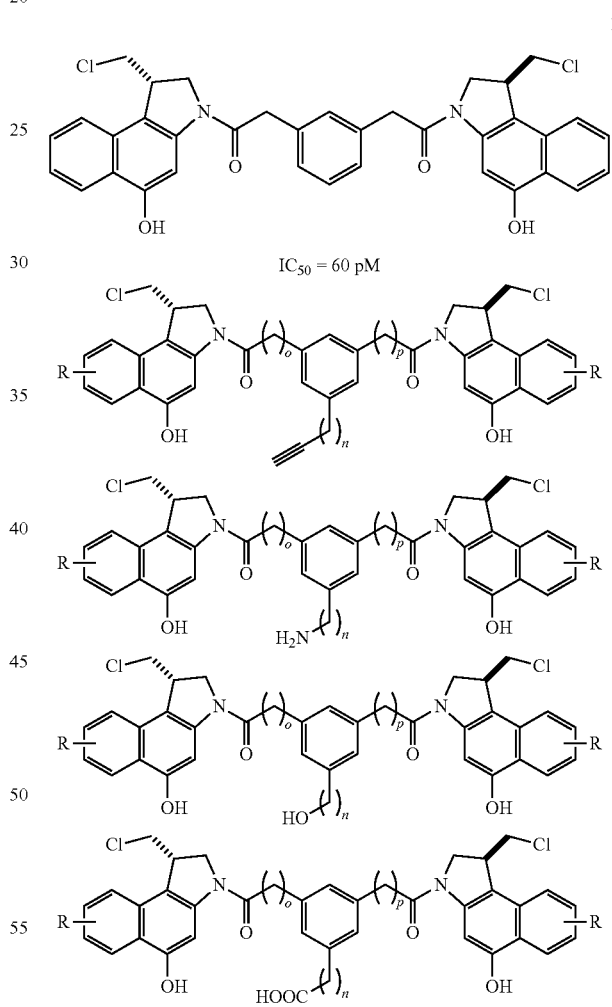

where n is an integer from 0 to 10 and o and p is an integer from 0 to 5; the chains may additionally contain one or two oxygen atoms, one or two nitrogen atoms with an alkyl or aryl group, or one or two sulfur atoms.

Other bifunctional CBI derivatives as well, with, for example, an N atom in the chain which links the two CBI units, can be used in order to insert monoclonal antibodies,

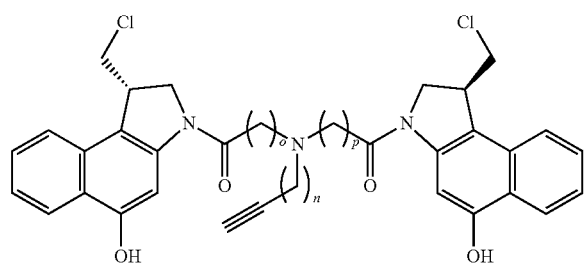

IC$_{50}$ = 110 pM (o = p = n = 1)

where n is an integer from 0 to 10 and o and p is an integer from 0 to 5; the chains ( )$_o$ and ( )$_p$ may additionally contain one or two oxygen atoms, one or two nitrogen atoms with an alkyl or aryl group, or one or two sulfur atoms.

All compounds can be detoxified by means, for example, of benzylation or glycosidation of the phenolic hydroxyl groups. The toxins are then released in the lysosome by oxidative cleavage with P 450 or by reaction with a glycohydrolase:

b) attachment of a monoclonal antibody via the benzene ring of a benzyl protective bifunctional duocarmycin derivative. The advantage of this approach is that on elimination of the benzyl group with the antibody by P450 in the lysosome, the primary compound is released with an IC$_{50}$=150 fM (R=H, r=1). Moreover, the compounds are stable in the serum and the conjugates display a very low toxicity.

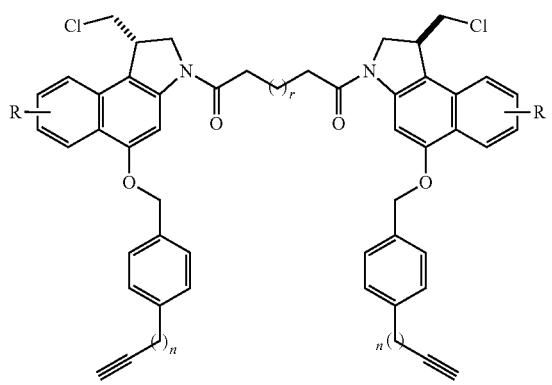

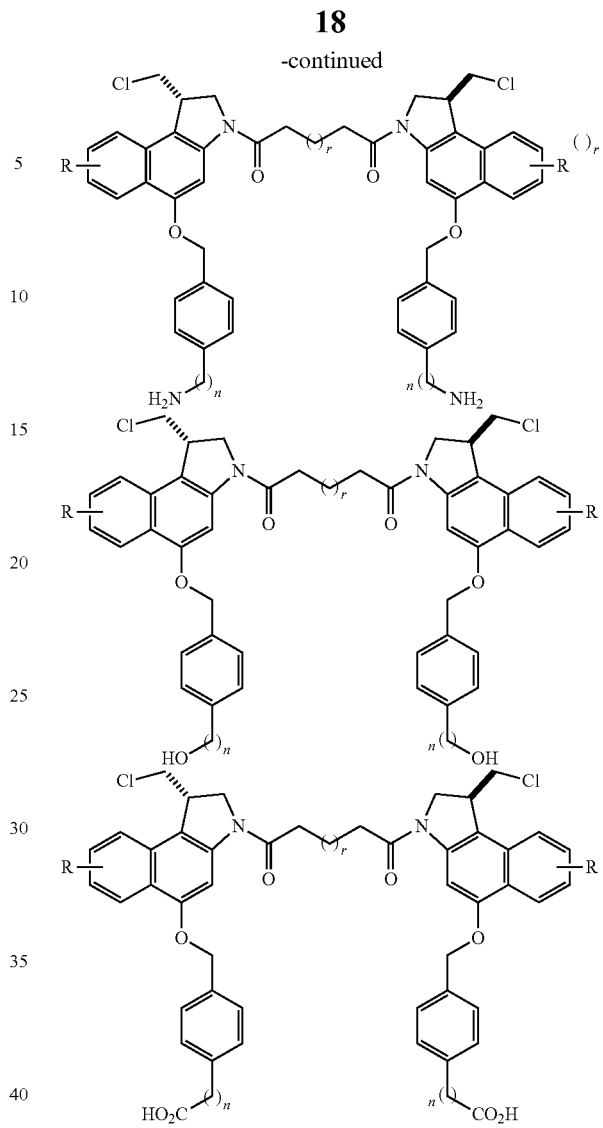

c) attachment of a monoclonal antibody via an acid-labile sugar acetal of a glycolized bifunctional duocarmycin derivative. The advantage of this approach is that on acid-catalyzed cleavage of the acetal with the antibody, and the elimination of the sugar component by glycohydrolases in the lysosome, the primary compound is released with an IC$_{50}$=150 fM. Moreover, the compounds are stable in the serum and the conjugates display a very low toxicity.

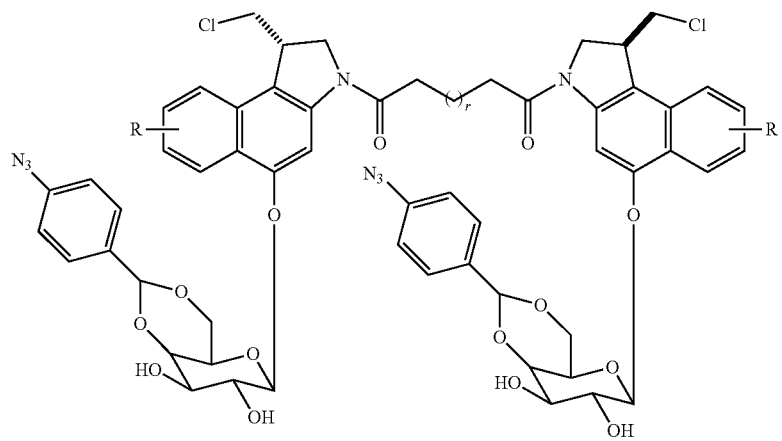

In the compounds, r may be an integer of 0-5, the radical ( )$_r$ may, moreover, contain one or two oxygen atoms, one or two sulfur atoms, or one or two NR$_Z$ groups, where R$_Z$ is as defined above. Alternatively, the radical ( )$_r$ may be a radical Y, as defined above.

In order to have the possibility of attachment of the dimeric duocarmycin derivatives, dicarboxylic acid components were developed which carry, centrally, a functionality. The functionality may be an alkyne group, an amino group, an OH group, an SH group, or a polyglycine group. There are numerous techniques known for attaching functionalities of these kinds to monoclonal antibodies.

The following substances are suitable for attachment to tumor-specific monoclonal antibodies: therein, R may be an alkyl of 0 to 5 atoms, halogen, OH, C0 to C5 alkoxy, N—C0 to C5 alkyl and/or S—C0 to C5 alkyl and/or S-aryl.

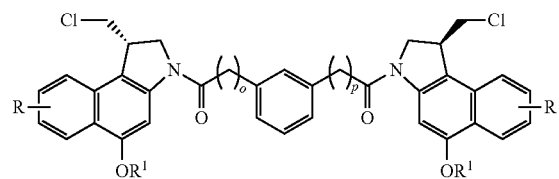

R$^1$ = H, o, p = 0-5 (1)
R$^1$ = sugar, benzyl, substituted benzyl, alkyl, acetal, o, p = 0-5 (2)

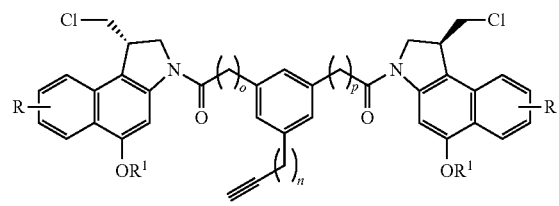

R$^1$ = H, n = 0-10, o, p = 0-5: (3)
R$^1$ = sugar, benzyl, substituted benzyl, alkyl, acetal: n = 0-10, o, p = 0-5 (4)

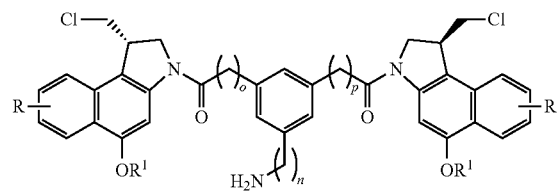

R$^1$ = H, n = 0-10, o, p = 0-5: (5)
R$^1$ = sugar, benzyl, substituted benzyl, alkyl, acetal: n = 0-10, o, p = 0-5 (6)

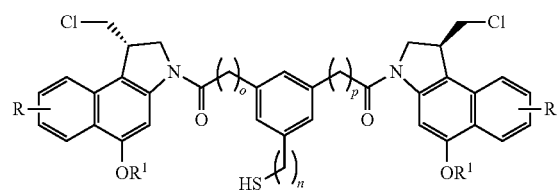

R$^1$ = H, n = 0-10, o, p = 0-5: (7)
R$^1$ = sugar, benzyl, substituted benzyl, alkyl, acetal: n = 0-10, n$^1$ = 0-5 (8)

-continued

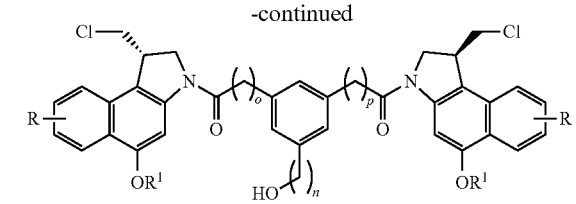

R$^1$ = H, n = 0-10, o, p = 0-5: (9)
R$^1$ = sugar, benzyl, substituted benzyl, alkyl, acetal: n = 0-10, o, p = 0-5 (10)

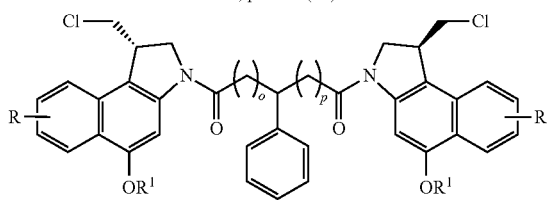

R$^1$ = H, n = 0-10, o, p = 0-5: (11)
R$^1$ = sugar, benzyl, substituted benzyl, alkyl, acetal: n = 0-10, o, p = 0-5 (12)

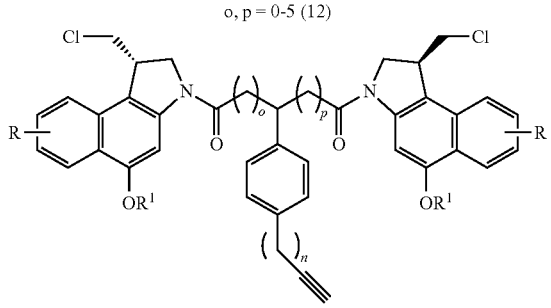

R$^1$ = H, n = 0-10, o, p = 0-5: (13)
R$^1$ = sugar, benzyl, substituted benzyl, alkyl, acetal: n = 0-10, o, p = 0-5 (14)

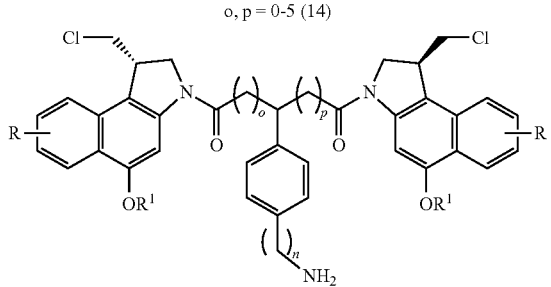

R$^1$ = H, n = 0-10, o, p = 0-5: (15)
R$^1$ = sugar, benzyl, substituted benzyl, alkyl, acetal: n = 0-10, o, p = 0-5 (16)

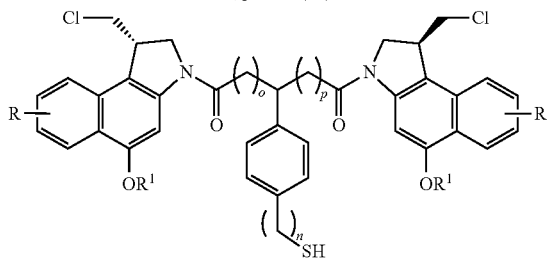

R$^1$ = H, n = 0-10, o, p = 0-5: (17)
R$^1$ = sugar, benzyl, substituted benzyl, alkyl, acetal: n = 0-10, o, p = 0-5 (18)

-continued

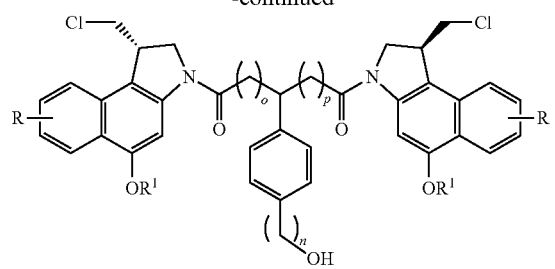

R¹ = H, n = 0-10, o, p = 0-5: (27)
R¹ = sugar, benzyl, substituted benzyl, alkyl, acetal: n = 0-10, o, p = 0-5 (28)

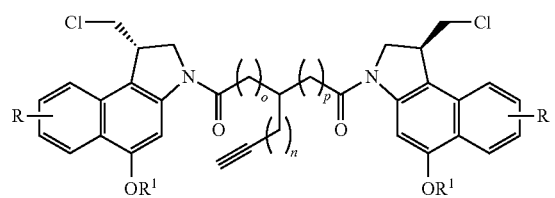

R¹ = H, n = 0-10, o, p = 0-5: (29)
R¹ = sugar, benzyl, substituted benzyl, alkyl, acetal: n = 0-10, o, p = 0-5 (30)

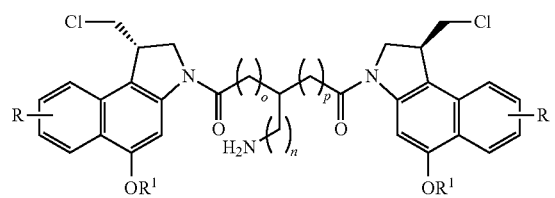

R¹ = H, n = 0-10, o, p = 0-5: (31)
R¹ = sugar, benzyl, substituted benzyl, alkyl, acetal: n = 0-3, n¹ = 0-3 (32)

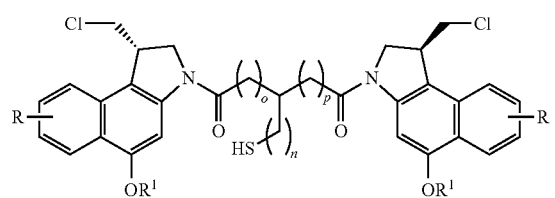

R¹ = H, n = 0-10, o, p = 0-5: (33)
R¹ = sugar, benzyl, substituted benzyl, alkyl, acetal: n = 0-3, o, p = 0-5 (34)

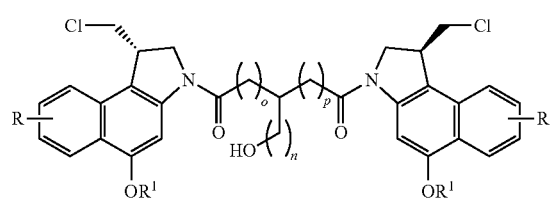

R¹ = H, n = 0-10, o, p = 0-5: (35)
R¹ = sugar, benzyl, substituted benzyl, alkyl, acetal: n = 0-10, o, p = 0-5 (36)

-continued

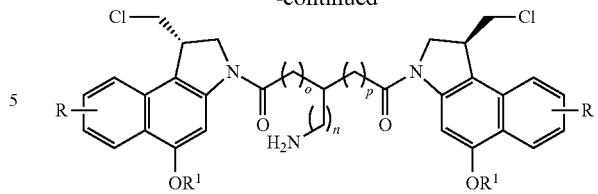

R¹ = H, n = 0-10, o, p = 0-5: (37)
R¹ = sugar, benzyl, substituted benzyl, alkyl, acetal: n = 0-10, o, p = 0-5 (38)

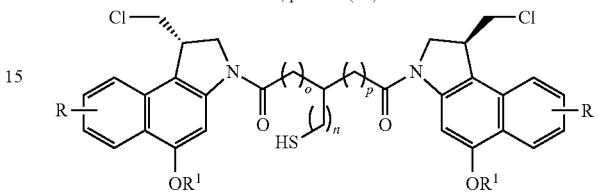

R¹ = H, n = 0-10, o, p = 0-5: (39)
R¹ = sugar, benzyl, substituted benzyl, alkyl, acetal: n = 0-10, o, p = 0-5 (40)

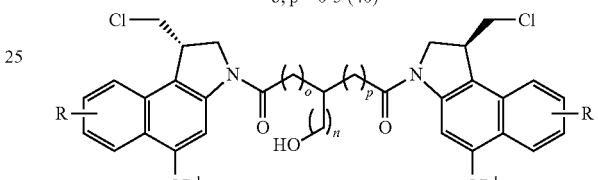

R¹ = H, n = 0-10, o, p = 0-5: (41)
R¹ = sugar, benzyl, substituted benzyl, alkyl, acetal: n = 0-10, o, p = 0-5 (42)

Described, finally, is the use of a compound of the invention or of an antibody-compound conjugate of the invention for treating tumoral diseases, especially in mammals.

In accordance with the invention it is possible to utilize the compounds and antibody-compound conjugates described in order to introduce the prodrugs into the target cells or the target tissue in order there to operate a tumor treatment or to treat precursors thereof.

The tumoral diseases include, in particular, solid tumors.

EXPERIMENTAL SECTION 2,2'-(1,3-Phenylene)bis(1-((S)-1-(chloromethyl)-5-hydroxy-1,2-dihydro-3H-benzo[e]indol-3-yl)ethan-1-one) (2)

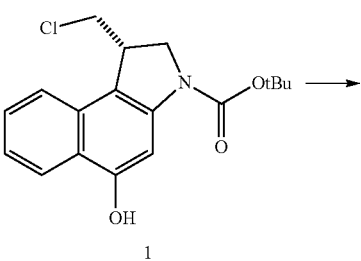

1

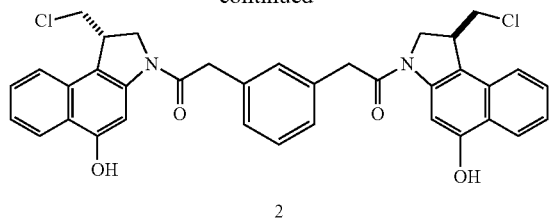

4M HCl/EtOAc (12 ml) was added to the CBI derivative 1 (100 mg, 300 µmol, 1.0 eq.) and the mixture was stirred at room temperature for 4 h, after which the excess of HCl/EtOAc was removed by application of a high vacuum for 1 h. The residue was dissolved in DMF (12 ml) and pyridine (48 µl, 600 µmol, 2.0 eq.), then admixed at 0° C. with 2,2'-(1,3-phenylene)diacetyl chloride (34 mg, 150 µmol, 0.5 eq.), and the resulting mixture was stirred at room temperature for 12 h. The solvent was removed under reduced pressure on a rotary evaporator and the residue was purified by chromatography on silica gel (MeOH/CH$_2$Cl$_2$ 1:19). Further purification took place by preparative TLC (TLC (MeOH/CH$_2$Cl$_2$ 1:40) and preparative HPLC. The desired product 2 was obtained as a white foam (16 mg, 25.6 µmol, 17%).

R$_f$: 0.5 (MeOH/CH$_2$Cl$_2$ 1:19).

Optical rotation: $[\alpha]_D^{20}$=–22.0 (c 0.5, DMSO).

IR(KBr): ν [cm$^{-1}$]=3182, 2360, 1635, 1584, 1421, 1391, 1250, 1133, 857, 772, 754, 715.

$^1$H-NMR (300 MHz, CDCl$_3$): δ [ppm]=2.58 (t, J=9.0 Hz, 2H, 2'-H$_a$, 6'-H$_a$), 2.99 (t, J=9.0 Hz, 2H, 2'-H$_b$, 6'-H$_b$), 3.54 (dd, J=9.0, 3.0 Hz, 2H, 2×10-H$_a$), 3.68 (t, J=9.0 Hz, 2H, 2×10-H$_b$), 3.75-4.04 (m, 6H, 2×1-H, 2×2-H$_a$, 2×2-H$_b$), 7.08 (d, J=9.0 Hz, 2H, 2×9-H), 7.28-7.37 (m, 4H, 2×7-H, 2×15-H), 7.42-7.47 (m, 2H, 2×8-H), 7.59 (t, J=9.0 Hz, 1H, 16-H), 7.93 (s, 3H, 2×4-H, 14-H), 8.0 (d, J=6.0 Hz, 2H, 6-H), 9.91 (bs, 2H, 2×OH). $^{13}$C-NMR (125 MHz, CDCl$_3$): δ [ppm]= 41.2 (2×C-1), 43.4 (2×C-12), 46.4 (2×C-10), 53.3 (2×C-2), 100.2 (2×C-4), 113.9 (2×C-2), 122.1 (2×C-9), 122.2 (2×C-9$_b$), 122.9 (2×C-7), 123.2 (2×C-6), 126.3 (2×C-8), 128.7 (2×C-15), 129.0 (C-16), 129.3 (2×C-9$_a$), 130.6 (C-14), 133.8 (2×C-13), 140.6 (2×C-3), 154.4 (2×C-5), 170.3 (2×C=O).

MS (ESI): m/z (%) 647.2 [M+Na]$^+$(100).

C$_{36}$H$_{30}$Cl$_2$N$_2$O$_4$ (624.16) calc.: 623.1510 found.: 623.1502, [M–H]$^-$ (ESI-HRMS).

HPLC (analytical):

Column: Kromasil® 100 C18, 250×4 mm, 5 µm

Mobile phase: 30/70 H$_2$O/MeOH

Flow rate: 0.8 ml min$^{-1}$

λ=254 nm t$_R$: 3.4 min

1,5-bis((S)-1-(Chloromethyl)-5-hydroxy-1,2-dihydro-3H-benzo[e]indol-3-yl)-3-phenylpentane-1,5-dione (3)

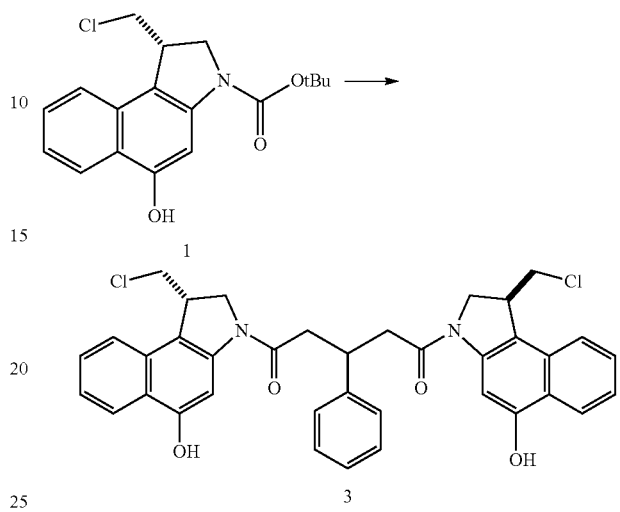

4M HCl/EtOAc (6 ml) was added to the CBI derivative 1 (50 mg, 150 µmol, 1.0 eq.) and the mixture was stirred at room temperature for 4 h, after which the excess of HCl/EtOAc was removed by application of a high vacuum for 1 h. The residue was dissolved in DMF (6 ml) and pyridine (24 µl, 300 µmol, 2.0 eq.), then admixed at 0° C. with 3-phenylpentanedioyl dichloride (15 mg, 60 µmol, 0.4 eq.), and the resulting mixture was stirred at room temperature for 12 h. The solvent was removed under reduced pressure on a rotary evaporator and the residue was purified by chromatography on silica gel (EtOAc/Hex 1:1). Further purification took place by preparative HPLC. The desired product 3 was obtained as a white foam (30 mg, 47 µmol, 78%).

R$_f$: 0.6 (EtOAc/Hex 1:1).

Optical rotation: $[\alpha]_D^{20}$=–26.6 (c 0.82, DMSO).

IR (KBr): ν [cm$^{-1}$]=3122, 2360, 1630, 1583, 1422, 1392, 1255, 1132, 856, 756, 718, 700.

$^1$H-NMR (300 MHz, CDCl$_3$): δ [ppm]=2.27-2.35 (bm, 0.5H$_{minor}$, 12-H$_a$), 2.53-2.74 (bm, 1.5H, 12-H$_a$) 2.81-3.17 (m, 4H, 2×12-H$_b$, 2×1-H), 3.22-3.47 (m, 2H, 2×10-H$_a$), 3.48-3.66 (m, 2H, 2×10-H$_b$), 3.74-4.04 (m, 2H, 2×2-H$_a$), 4.06-4.39 (m, 2H, 2×2-H$_b$), 4.58 (t, J=9.0 Hz, 0.3H$_{minor}$, 13-H), 4.76 (t, J=9.0 Hz, 0.7H, 13-H), 6.74 (bd, J=6.0 Hz, 1H, 17-H), 6.87-7.17 (m, 2H, 2×16-H), 7.31-7.46 (m, 5H, 2×7-H, 2×9-H, 8-H), 7.47-7.59 (bm, 3H, 8-H, 2×15-H), 8.04-8.39 (m, 4H, 2×4-H, 2×6-H), 10.23 (bs, 0.6H, OH), 10.50 (bs, 0.4H$_{minor}$, OH), 10.80 (bs, 0.2H$_{minor}$, OH), 11.32 (bs, 0.8H, OH).

$^{13}$C-NMR (125 MHz, CDCl$_3$): δ [ppm]=35.7 (C-13), 40.6 (2×C-1$_{minor}$), 41.0 (2×C-1), 41.3 (2×C-1'), 45.8 (2×C-12), 45.9 (2×C-12$_{minor}$), 46.3 (2×C-12'), 46.7 (2×C-10), 46.8 (2×C-10$_{minor}$), 47.0 (2×C-10'), 53.4 (2×C-2), 53.6 (2×C-2$_{minor}$), 53.9 (2×C-2'), 54.1 (2×C-2'$_{minor}$), 101.0 (2×C-4$_{minor}$), 101.3 (2×C-4), 101.7 (2×C-4'), 102.1 (2×C-4'$_{minor}$), 114.1 (2×C-2$_{minor}$), 114.5 (2×C-2), 114.6 (2×C-2'), 115.2 (2×C-2'$_{minor}$), 121.9 (2×C-9$_{b\ minor}$), 122.1 (2×C-9$_b$), 122.3 (2×C-7), 122.4 (2×C-7'), 122.7 (2×C-6), 122.9 (2×C-6'), 123.0 (2×C-9), 123.3 (2×C-9'), 126.3 (C-17), 126.4 (2×C-15), 126.5 (2×C-8), 127.2 (2×C-16), 129.3 (2×C-9$_a$), 129.4 (2×C-16'), 140.3 (2×C-3), 140.6 (2×C-3$_{minor}$), 140.8 (2×C-

Figure 3:
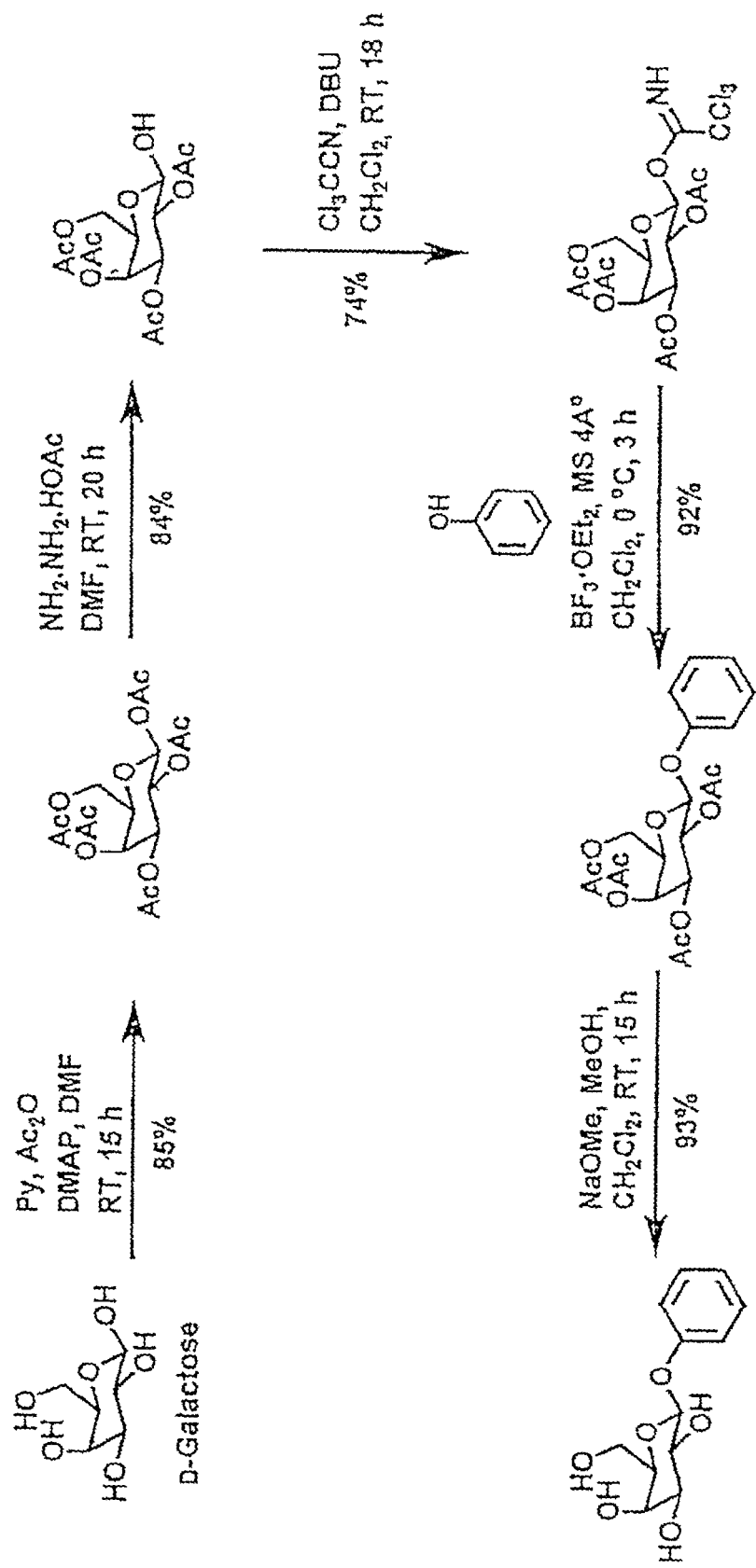
FIG. 3. Synthesis of a precursor of bifunctional seco-CBI glycosides.
Figure 4:
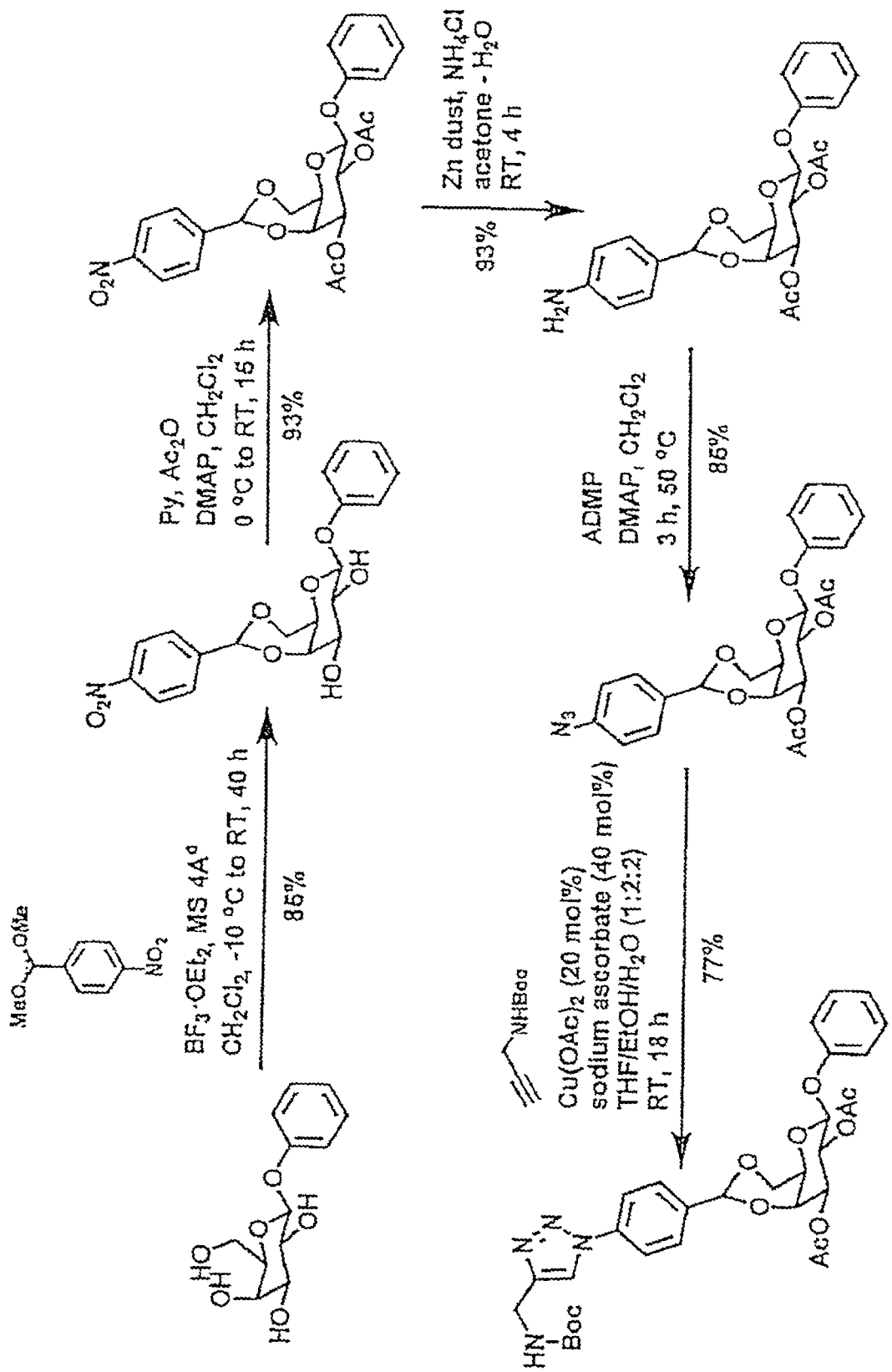
FIG. 4. Synthesis of a precursor of bifunctional seco-CBI glycosides.

3'$_{minor}$), 141.2 (2×C-3'), 146.0 (C-14), 146.4 (C-14$_{minor}$), 153.3 (2×C-5), 153.6 (2×C-5$_{minor}$), 154.2 (2×C-5'$_{minor}$), 154.6 (2×C-5'), 169.5 (2×C=O$_{minor}$), 169.7 (2×C=O), 171.0 (2×C=O$_{minor}$), 171.1 (2×C=O), MS (ESI): m/z (%) 661.2 [M+Na]+(100).
$C_{37}H_{32}Cl_2N_2O_4$ (661.2) calc.: 661.1637.
found.: 661.1618, [M+Na]$^+$.
(ESI-HRMS).
HPLC (analytical):
Column: Kromasil® 100 C18, 250×4 mm, 5 μm
Mobile phase: 30/70 $H_2O$/MeOH
Flow rate: 0.8 ml min$^{-1}$
λ=254 nm
t$_R$: 21.1 min The attached FIGS. 3 and 4 show the synthesis of a precursor of bifunctional seco-CBI glycosides. Represented is the formation of the acetals on the sugar and formation of a triazole group to protect the azide group, the azide group being suitable for later forming, with the antibody, a corresponding antibody-compound conjugate.

Figure 6:
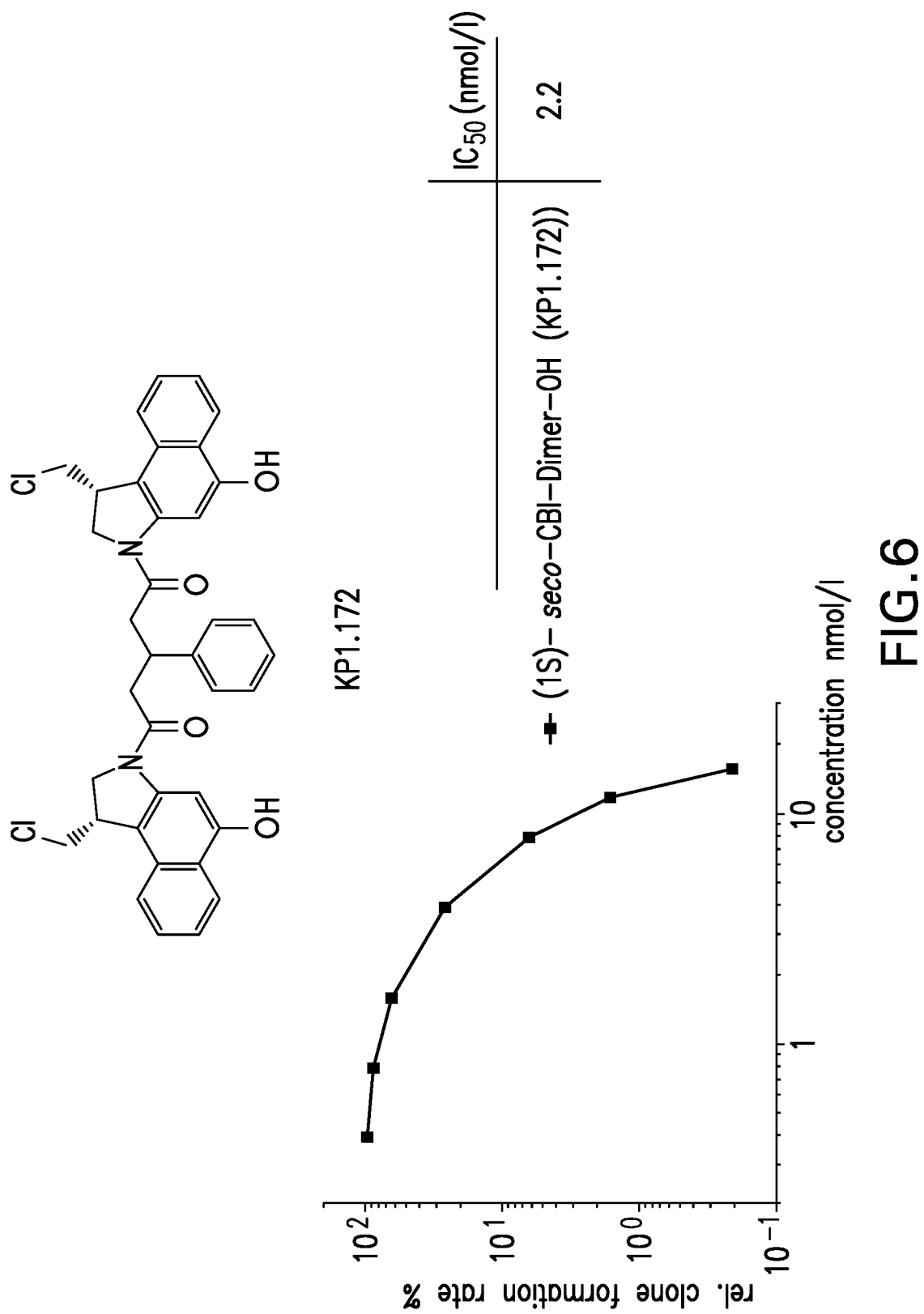
FIG. 6. Examples of structures according to the invention and their cytotoxicity in vitro in human bronchial carcinoma cells of line A549.
Figure 7:
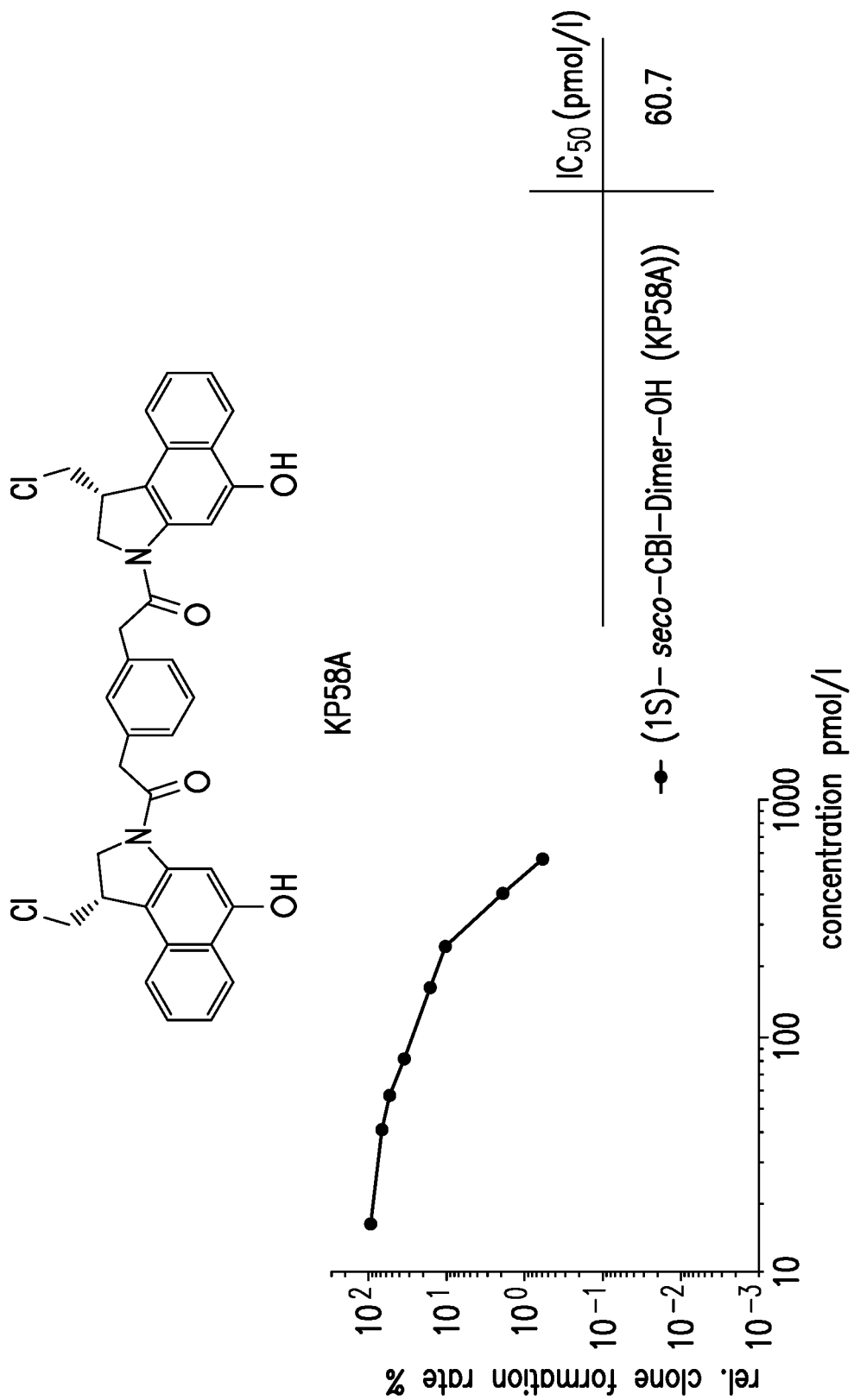
FIG. 7. Examples of structures according to the invention and their cytotoxicity in vitro in human bronchial carcinoma cells of line A549.
Figure 8:
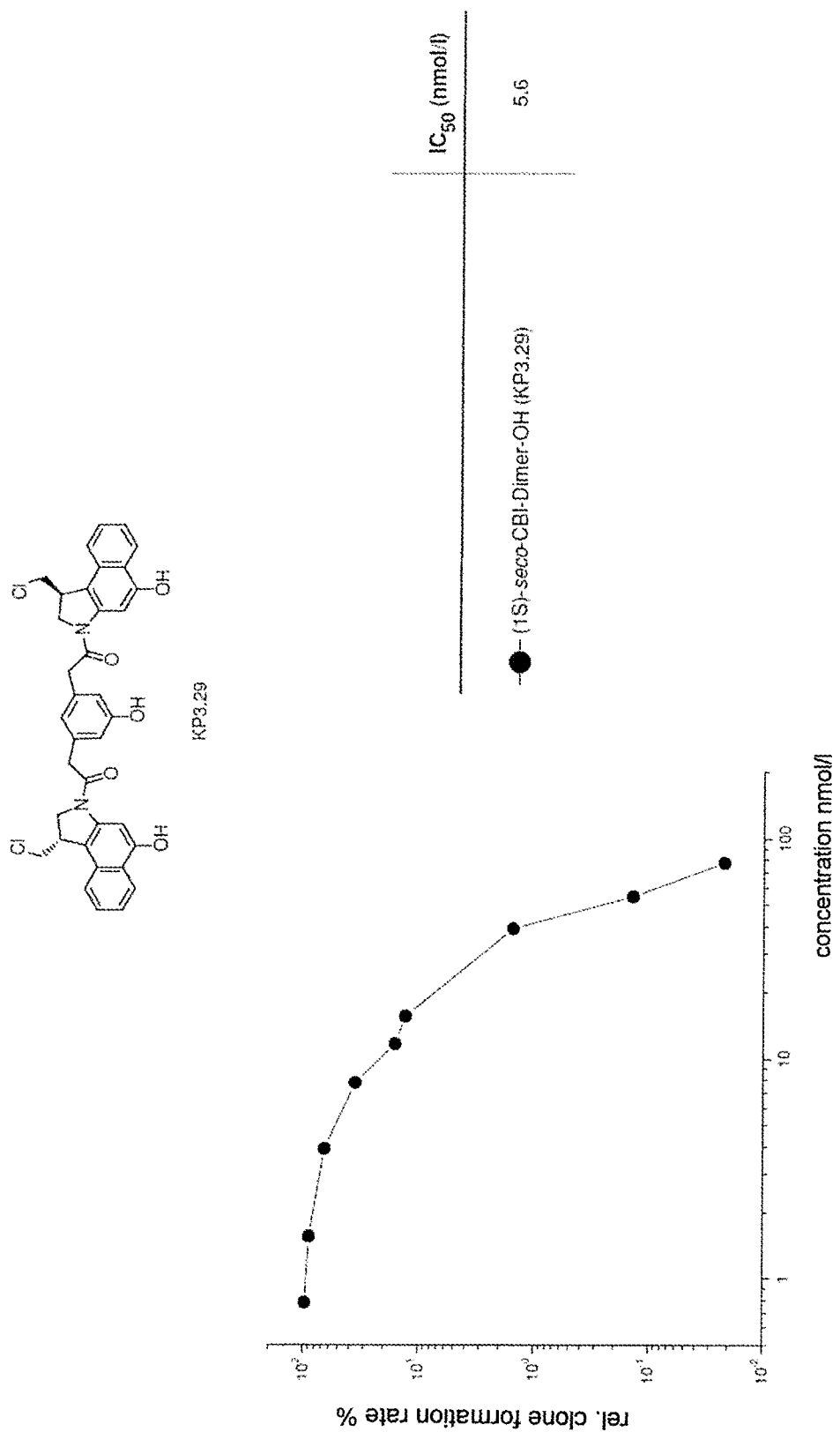
FIG. 8. In vitro toxicity of a synthesized compound in human bronchial carcinoma cells of line A549.
Figure 9:
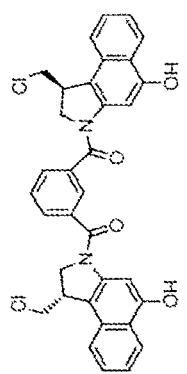
FIG. 9. In vitro toxicity of a synthesized compound in human bronchial carcinoma cells of line A549.
Figure 9:
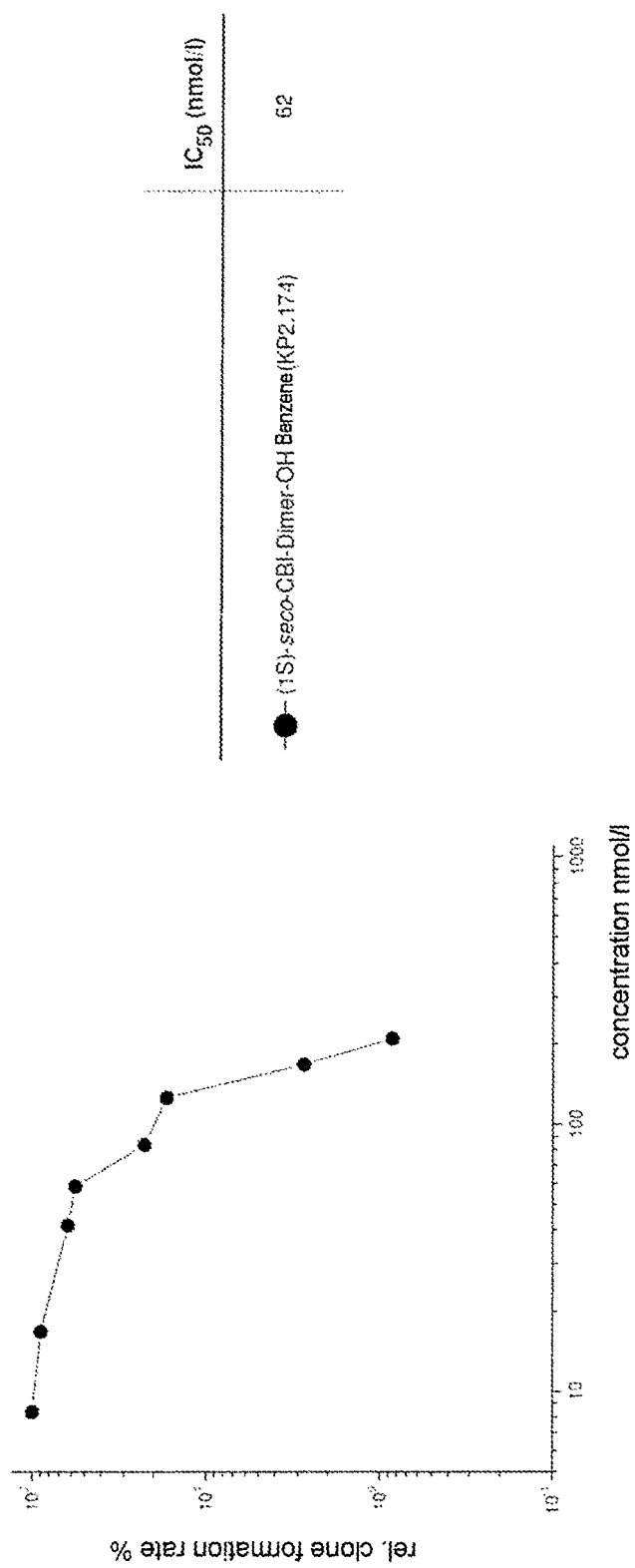
Figure 10:
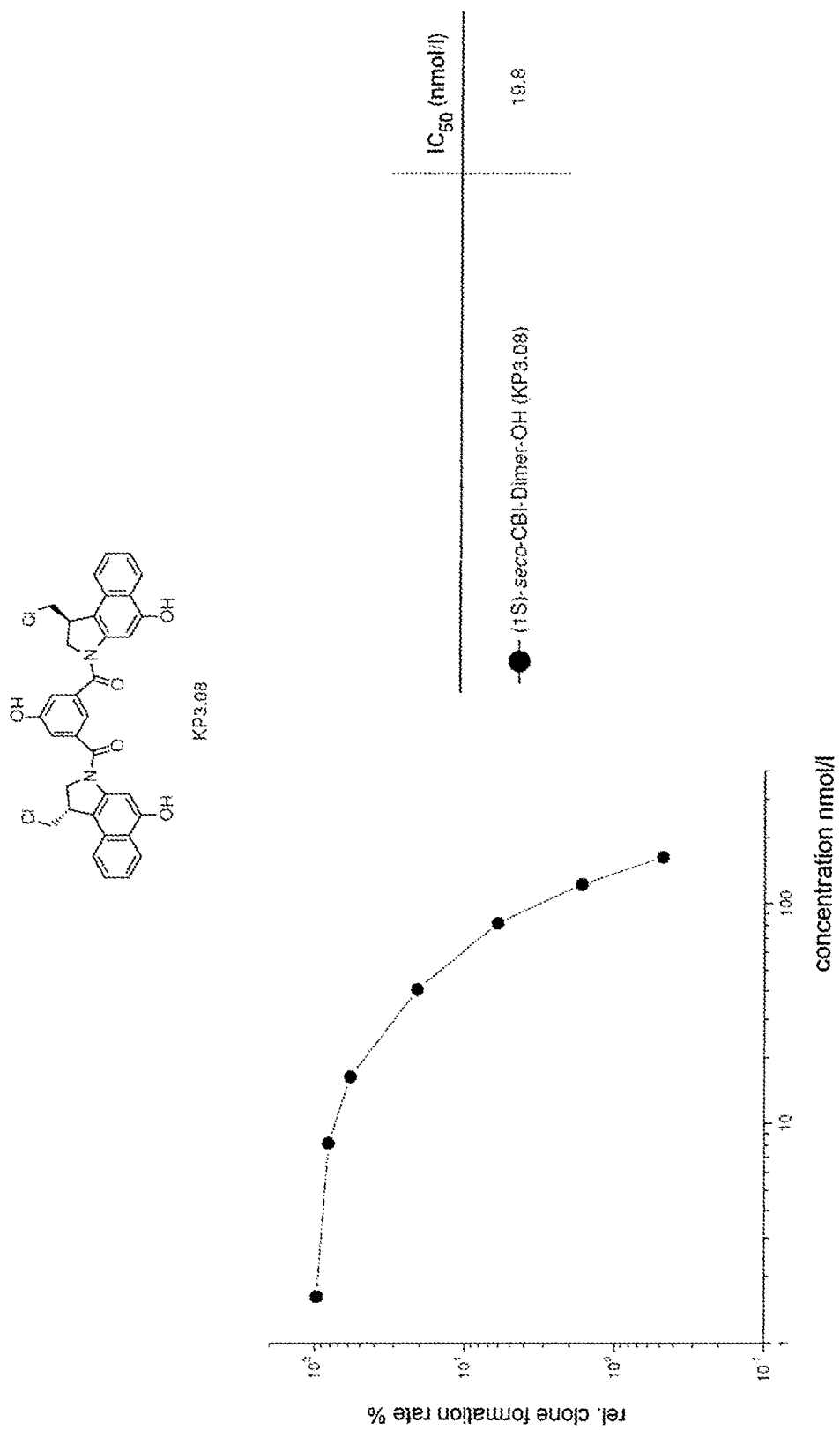
FIG. 10. In vitro toxicity of a synthesized compound in human bronchial carcinoma cells of line A549.
Figure 11:
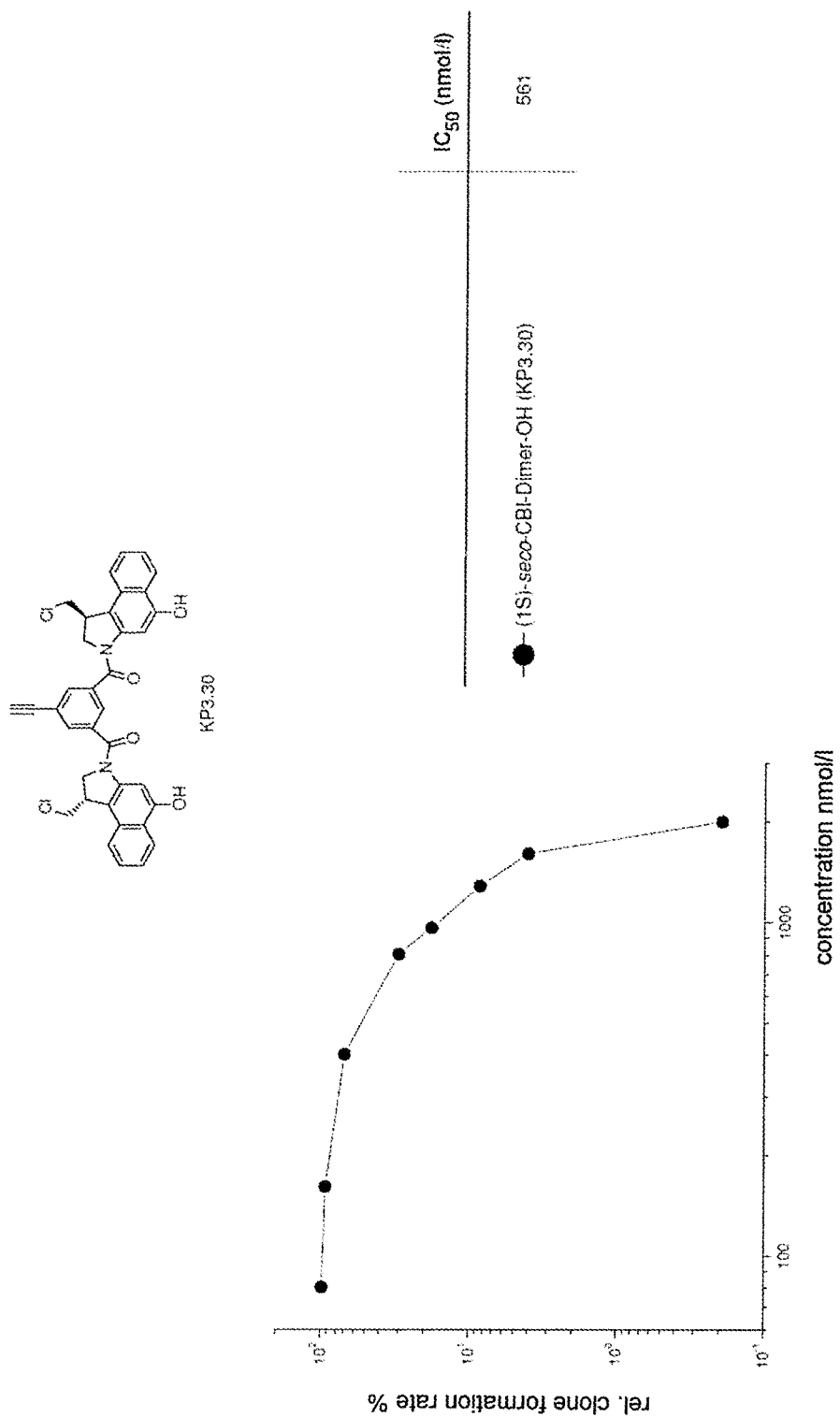
FIG. 11. In vitro toxicity of a synthesized compound in human bronchial carcinoma cells of line A549.
Figure 12:
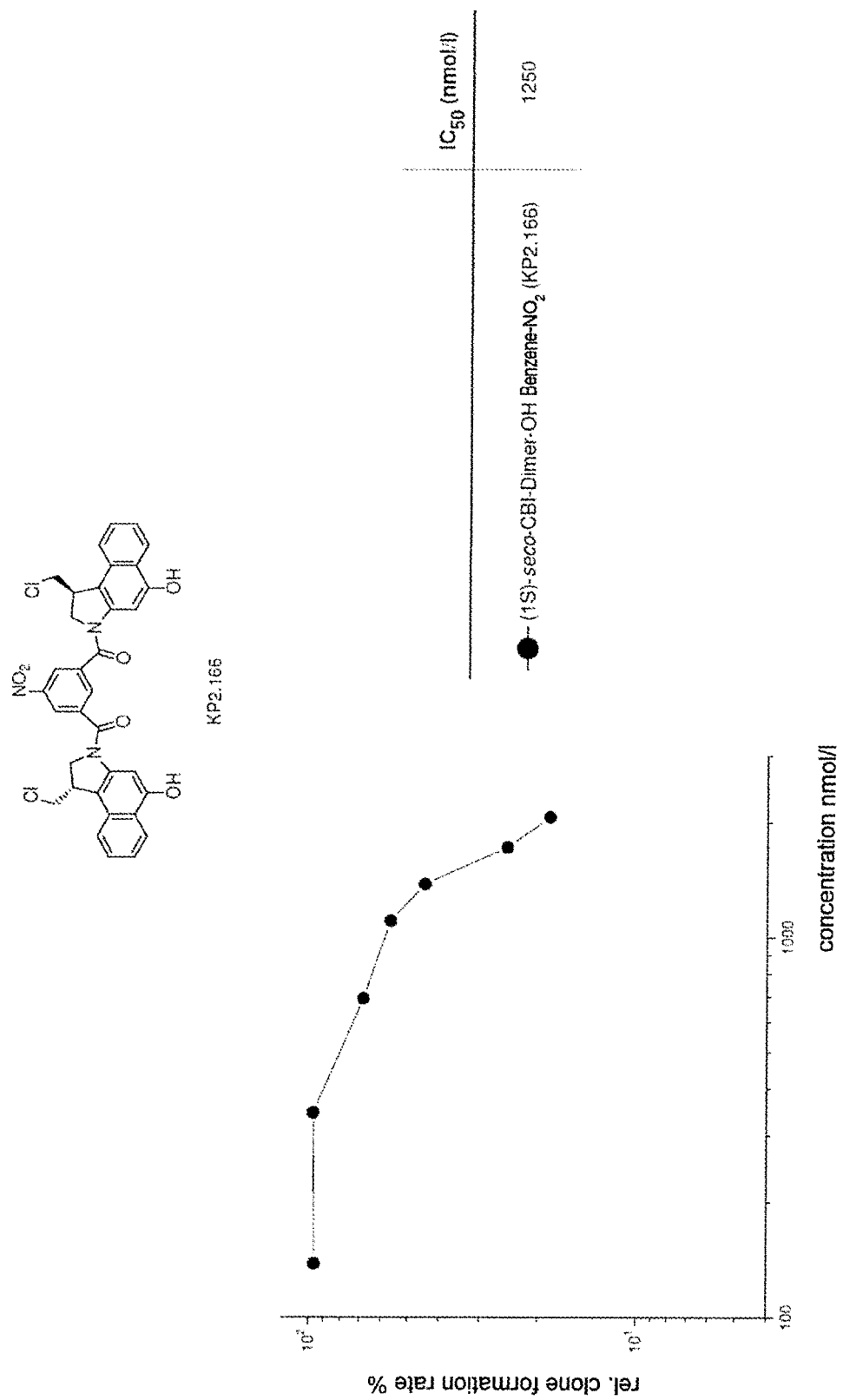
FIG. 12. In vitro toxicity of a synthesized compound in human bronchial carcinoma cells of line A549.
Figure 13:
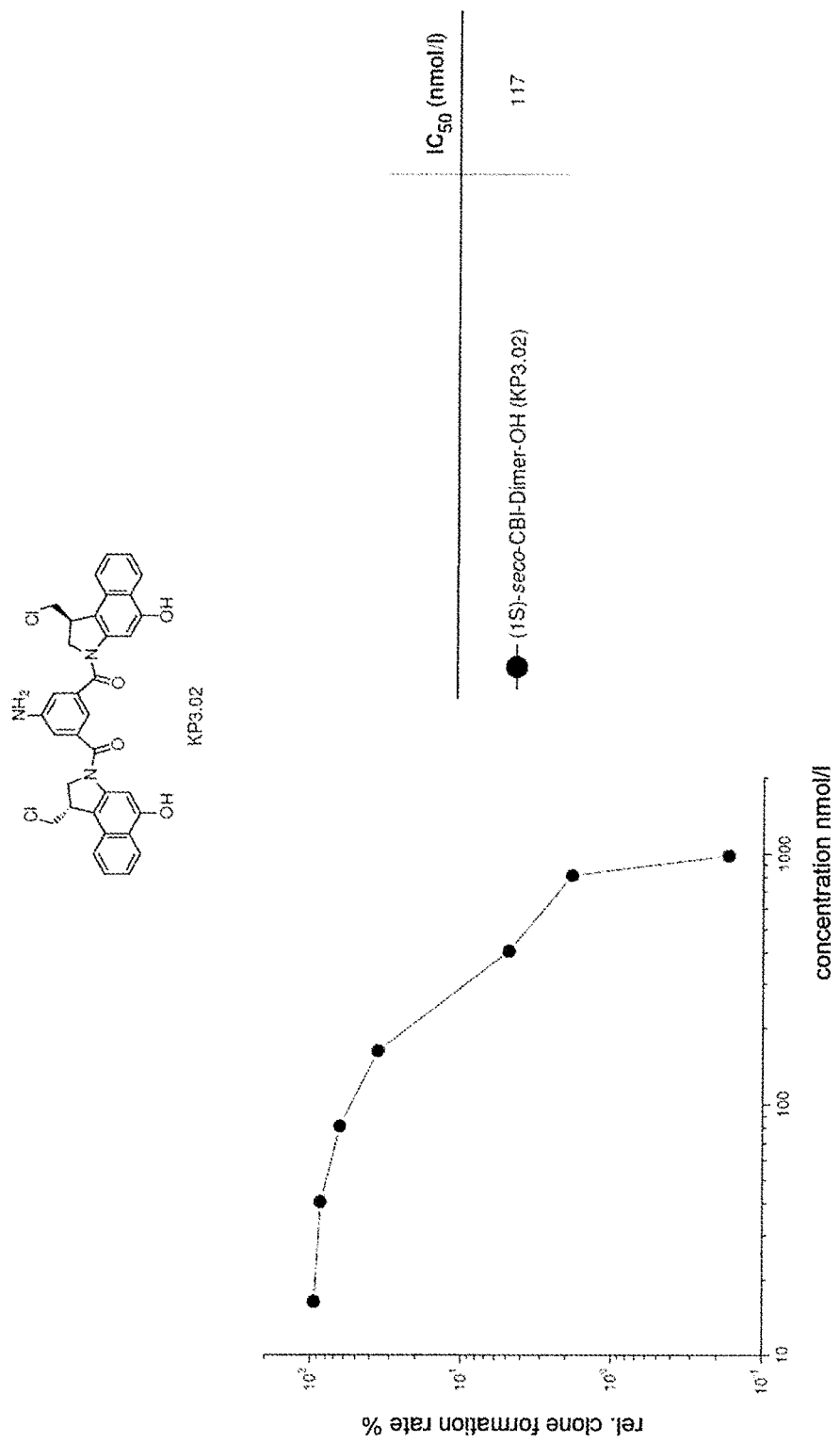
FIG. 13. In vitro toxicity of a synthesized compound in human bronchial carcinoma cells of line A549.
Figure 14:
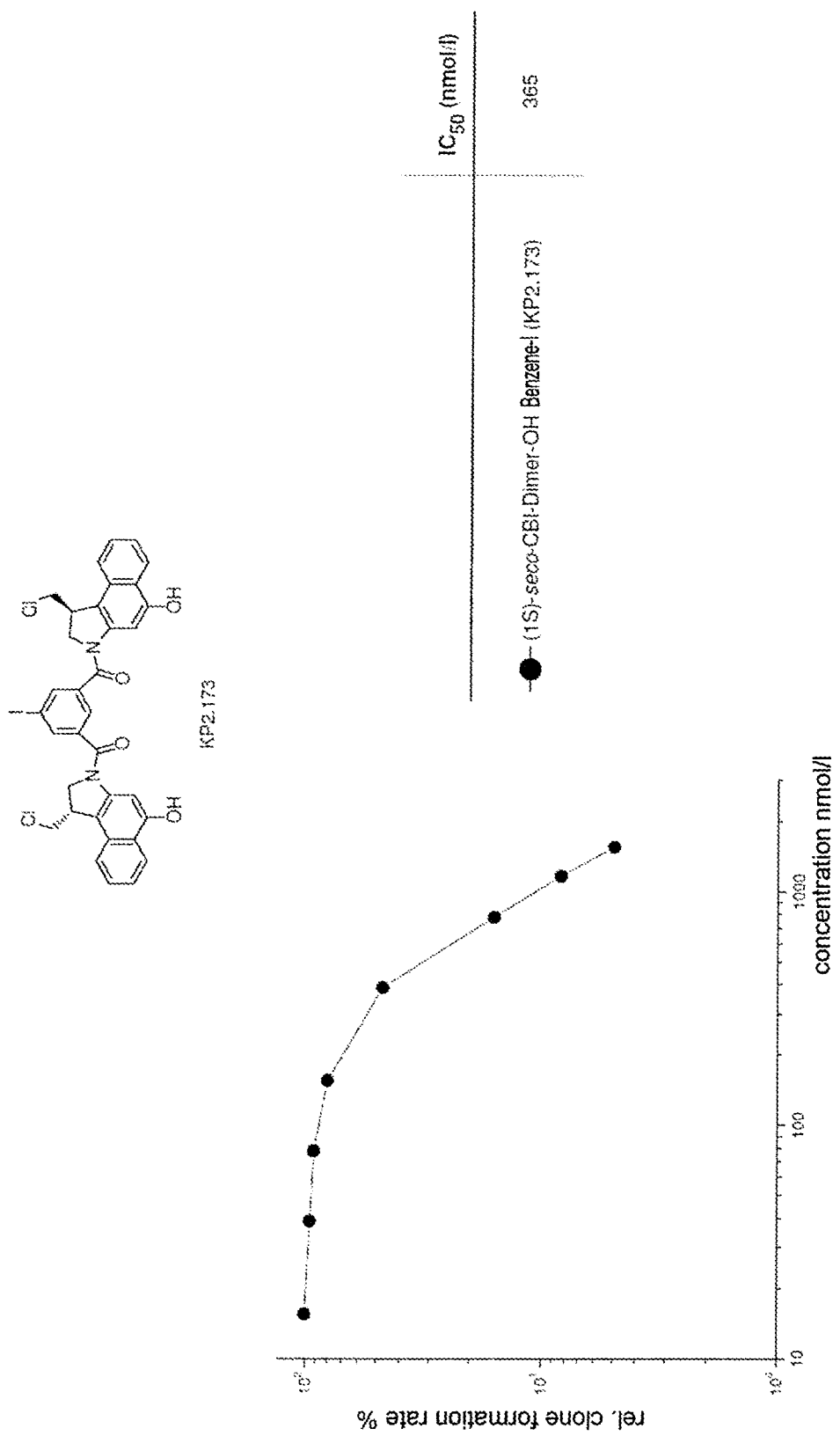
FIG. 14. In vitro toxicity of a synthesized compound in human bronchial carcinoma cells of line A549.

FIGS. 6 and 7 show the examples of structures according to the invention and their cytotoxicity in vitro in human bronchial carcinoma cells of line A549.

FIG. 5 shows a suitable structure of an antibody-compound conjugate. In this case, MAB (1) and MAB (2), respectively, show that different antibodies can be inserted. The attachment here is via a succinimide derivative. This compound represents an example of suitable linking of the compound of the invention to an antibody via a cleavable substrate.

General Methods
Experimental Methods:

Unless otherwise stated, the reactions were carried out under an inert gas atmosphere in flame-dried vessels and the reaction materials were introduced by syringe or transfer cannula under argon pressure. All solvents were of analytical purity and were stored over molecular sieve. All reagents obtained from commercial sources were used without further purification. Long-term cooling was carried out using a Haake EK 90 cryostat. Thin-layer chromatography was carried out using precoated silica gel plates SI 60 F$_{254}$ from Merck. Silica gel 60 (0.040 0.063 mm) from Merck was used for the flash chromatography. Staining was carried out by means of phosphomolybdic acid hydrate from Sigma-Aldrich (in MeOH). Yields are based on isolated and purified compounds, unless otherwise stated.

NMR Spectroscopy:

NMR spectra were recorded using Varian Mercury-300, Unity-300 and Inova-600 spectrometers in CDCl$_3$ or CD$_3$OD or d$^6$-DMSO; chemical shifts are reported in ppm relative to tetramethylsilane (TMS), coupling constants J in hertz. The mobile phase signals were used as references and the chemical shifts were converted into the TMS scaling (CHCl$_3$: δ$_H$=7.26 ppm, δ$_C$=77.0 ppm; CD$_3$OD: δ$_H$=3.34 ppm, δ$_C$=49.86 ppm and d$^6$-DMSO: δ$_H$=2.54 ppm, δ$_C$=40.45 ppm). The first-order multiplicities were designated as follows: s (singlet), d (doublet), t (triplet), q (quartet), dd (doublet of doublets), and so on. Higher-order signals were designated as m (multiplet).

IR Spectroscopy:

IR spectra were recorded using Bruker Vektor 22 spectrometers;

UV Spectroscopy:

UV spectra were recorded using JASCO V-630 spectrometers,

Mass Spectrometry:

ESI-MS and ESI-HRMS spectra were recorded using Bruker Daltonik Apex IV.

Further Syntheses 1,3-Phenylenebis(((S)-1-(chloromethyl)-5-hydroxy-1,2-dihydro-3H-benzo[e]indol-3-yl)methanone) (51)

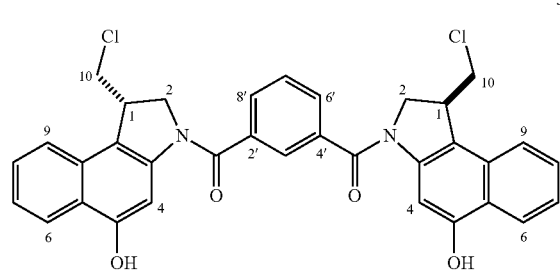

51

4M HCl/EtOAc (12 ml) was added to tbutoxycarbonylseco-CBI (50 mg, 150 μmol, 1.0 eq.) at room temperature and the mixture was stirred at the same temperature for three hours. Excess HCl/EtOAc was removed by evaporation under reduced pressure and drying was carried out under reduced pressure for one hour. The residue obtained was dissolved in DMF (12 ml) and admixed at 0° C. with pyridine (48 μl, 600 μmol, 4.0 eq.) followed by isophthaloyl dichloride (15 mg, 75 μmol, 0.5 eq.), and the reaction mixture was stirred at room temperature for 16 hours. Evaporation of the solvent under a high pressure gave a crude product which was purified by flash chromatography (EtOAc:PE 2:3 to EtOAc) in order to give 51 (38 mg, 85%).

R$_f$: 0.6 (EtOAc).

HPLC (analytical):

Column: Kromosil® 100 C18, 250×4 mm, 5 m

Mobile phase: MeOH/THF (1:1): $H_2O$=70:30

Flow rate: 0.8 ml min$^{-1}$

λ: 254 nm t$_R$: 9.6 min

Optical rotation: [α]$_D^{20}$=−35.0 (c 1.0, DMSO).

$^1$H-NMR (500 MHz, DMSO-d$_6$, 75° C.): δ [ppm]=3.88 (dd, J=11.0, 7.4 Hz, 2H, 2×10-H$_a$), 3.98 (dd, J=10.8, 3.1 Hz, 2H, 2×10-H$_b$), 4.05-4.23 (m, 4H, 2×1-H, 2×2-H$_a$), 4.38 (dd, J=9.0, 2.0 Hz, 2H, 2×2-H$_b$), 6.93 (d, J=0.8 Hz, 1H, 3'-H), 7.40 (ddd, J=8.1, 6.9, 1.1 Hz, 2H, 2×7-H), 7.55 (ddd, J=8.3, 6.8, 1.3 Hz, 2H, 2×8-H), 7.66 (brs, 1H, 4-H), 7.72-7.77 (m, 1H, 3'-H), 7.79-7.88 (m, 4H, 6'-H, 8'-H, 2×9-H), 7.91 (t, J=1.6 Hz, 1H, 4-H), 8.18 (d, J=8.1 Hz, 2H, 2×6-H), 10.24 (s, 2H, 2×5-OH).

$^{13}$C-NMR (126 MHz, DMSO-d$_6$, 75° C.): 3 [ppm]=41.4 (2×C-1), 47.8 (2×C-10), 55.9 (2×C-2), 100.7 (C-4), 116.0 (2×C-5a), 122.9 (2×C-9b), 123.2 (2×C-9), 123.6 (2×C-7), 123.8 (2×C-6), 125.4 (C-3'), 125.9 (C-4), 127.9 (2×C-8), 129.3 (C-6', C-8'), 129.7 (C-7'), 130.6 (2×C-9a), 137.9 (C-2', C-4'), 142.1 (2×C-3a), 154.8 (2×C-5), 167.7 (2×CON).

HRMS (ESI): m/z calculated for $C_{34}H_{26}Cl_2N_2O_4$ 619.1167 [M+Na]$^+$. found 619.1132.

5-Nitro-1,3-phenylene)bis(((S)-1-(chloromethyl)-5-hydroxy-1,2-dihydro-3H-benzo[e]indol-3-yl)methanone) (52)

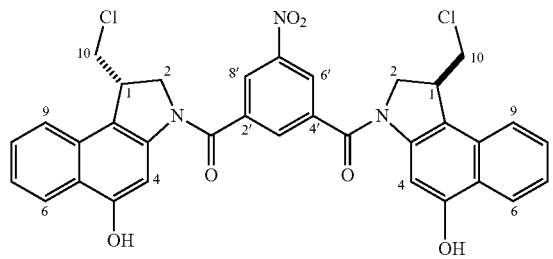

4M HCl/EtOAc (6 ml) was added to tbutoxycarbonylseco-CBI (50 mg, 150 μmol, 1.0 eq.) at room temperature and the resulting solution was stirred at the same temperature for 3 hours. Excess HCl/EtOAc was removed by evaporation under reduced pressure and the residue obtained was dried under a strong vacuum for 1 hour. The seco-CBI formed was dissolved in DMF (6 ml), which was admixed with stirring at 0° C. with pyridine (48 μl, 600 mol, 4.0 eq.) and 5-nitroisophthaloyl dichloride (20 mg, 75 mol, 0.5 eq.), and the stirring was continued at room temperature for 16 hours. Evaporation of the solvent under a high pressure gave the crude product, which was purified by flash chromatography (EtOAc:PE 1:1) to give 52 (44 mg, 88%).

$R_f$: 0.5 (EtOAc:PE=1:1).

HPLC (analytical):

Column: Kromosil® 100 C18, 250×4 mm, 5 m

Mobile phase: MeOH/THF (1:1): $H_2O$=70:30

Flow rate: 0.8 ml min$^{-1}$

λ: 254 nm $t_R$: 10.7 min

Optical rotation: $[\alpha]_D^{20}$=−6.6 (c 0.6, DMSO).

$^1$H-NMR (500 MHz, DMSO-$d_6$, 75° C.): δ [ppm]=3.87-4.05 (m, 4H, 2×10-$H_a$, 2×10-$H_b$), 4.07-4.27 (m, 4H, 2×1-H, 2×2-$H_b$), 4.40-4.57 (m, 2H, 2×2-$H_a$), 7.41 (ddd, J=8.1, 6.7, 1.1 Hz, 2H, 2×7-H), 7.56 (ddd, J=8.3, 6.8, 1.4 Hz, 3H, 2×8-H, 4-$H_b$), 7.76-7.97 (m, 3H, 2×9-H, 3'-H), 8.18 (d, J=8.3 Hz, 2H, 2×6-H), 8.37 (s, 1H, 4-$H_a$), 8.63 (d, J=1.5 Hz, 2H, 6'-H, 8'-H), 10.28 (s, 2H, 2×5-OH).

$^{13}$C-NMR (126 MHz, DMSO-$d_6$, 75° C.): δ [ppm]=41.5 (2×C-1), 47.8 (2×C-10), 55.7 (2×C-2), 100.4 (C-4a), 116.3 (2×C-5a), 123.1 (2×C-9a), 123.3 (2×C-9), 123.8 (2×C-7), 123.9 (2×C-6), 124.1 (C-7'), 125.4 (C-4$_b$), 128.0 (C-3'), 130.6 (2×C-8), 131.8 (2×C-9a), 139.4 (C-2', C-4'), 141.6 (2×C-3a), 148.9 (C-6', C-8'), 154.9 (2×C-5), 165.4 (2×CON).

HRMS (ESI): m/z calculated for $C_{34}H_{25}Cl_2N_3O_6$ 640.1042 [M−H]$^+$. found 640.1022.

5-Amino-1,3-phenylene)bis(((S)-1-(chloromethyl)-5-hydroxy-1,2-dihydro-3H-benzol[e]indol-3-yl)methanone) (53)

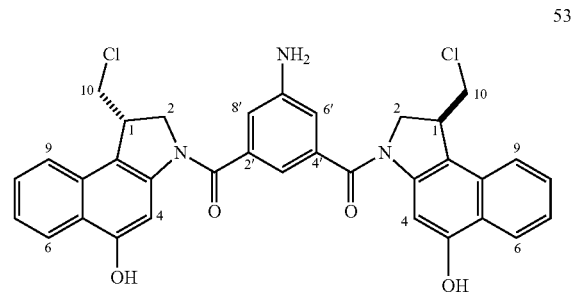 [SMILES: O=C(c1cc(C(=O)N2C[C@@H](CCl)c3c2cc(O)c2ccccc32)cc([N+](=O)[O-])c1)N1C[C@@H](CCl)c2c1cc(O)c1ccccc21]

Compound 52 ((18 mg, 28 μmol) was dissolved in THF (20 ml) and passed twice over H-Cube 10% Pd/C system under full $H_2$ mode at room temperature. After the end of the reaction, the solvent was evaporated under reduced pressure to give the crude product, which was then purified by flash column chromatography (MeOH:$CH_2Cl_2$ 1:4) to give 53 (13 mg, 76%).

$R_f$: 0.4 (EtOAc).

HPLC (analytical):

Column: Kromosil® 100 C18, 250×4 mm, 5 m

Mobile phase: MeOH/THF (1:1): $H_2O$=62:38

Flow rate: 0.8 ml min$^{-1}$

λ: 254 nm $t_R$: 19.8 min

Optical rotation: $[\alpha]D^{20}$=−27.5 (c 0.4, DMSO).

$^1$H-NMR (500 MHz, DMSO-$d_6$, 50° C.): δ [ppm]=3.46-4.26 (m, 8H, 2×10-$H_a$, 2×10-$H_b$, 2×1-H, 2×2-$H_a$), 4.40 (s, 2H, 2×2-$H_b$), 6.95 (s, 1H, 3'-H), 6.92 (d, J=1.0 Hz, 2H, 6'-H, 8'-H), 6.57 (d, J=1.0 Hz, 2$H_{minor}$, 6'-H, 8'-H) 7.30-7.45 (m, 2H, 2×7-H), 7.47-7.61 (m, 2H, 2×8-H), 7.62-8.07 (m, 4H, 2×9-H, 2×4-H), 8.08-8.28 (m, 2H, 2×6-H), 10.35 (s, 2H, 2×5-OH).

$^{13}$C-NMR (126 MHz, DMSO-$d_6$, 50° C.): δ [ppm]=40.9 (2×C-1), 48.1 (2×C-10), 56.0 (2×C-2), 100.8 (C-4), 114.5 (C-3'), 116.0 (2×C-5b), 122.9 (2×C-9b), 123.4 (2×C-7), 123.7 (C-6', C-8'), 123.9 (2×C-9), 125.6 (2×C-6), 128.0 (2×C-8), 128.7 (C-2', C-4'), 130.8 (2×C-9a), 139.9 (2×C-3a), 152.2 (C-7'), 154.9 (2×C-5), 168.6 (2×CON).

HRMS (ESI): m/z calculated for $C_{34}H_{27}Cl_2N_3O_4$ 634.1276 [M+Na]$^+$. found 634.1277.

5-Iodo-1,3-phenylene)bis(((S)-1-(chloromethyl)-5-hydroxy-1,2-dihydro-3H-benzo[e]indol-3-yl)methanone) (54)

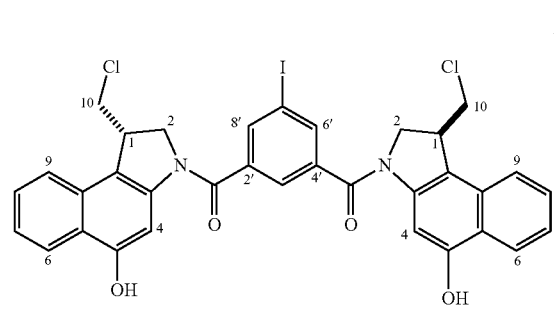

4M HCl/EtOAc (12 ml) was added to tbutoxycarbonylseco-CBI (50 mg, 150 µmol, 1.0 eq.) at room temperature and the mixture was stirred at the same temperature for 3 hours. Excess HCl/EtOAc was removed by evaporation under reduced pressure and the residue was dried under a strong vacuum for one hour. The resulting residue was dissolved in DMF (12 ml) and admixed with stirring at 0° C. with pyridine (48 µl, 600 µmol, 4.0 eq.) and 5-iodoisophthaloyl dichloride (24 mg, 75 µmol, 0.5 eq.). Stirring was continued at room temperature for 16 hours. After evaporation of the solvent under a high pressure, a crude product was obtained which was purified by flash chromatography (EtOAc:PE 1:1 to EtOAc) to give 54 (49 mg, 90%).

$R_f$: 0.3 (EtOAc:PE 1:1).

HPLC (analytical):

Column: Kromosil® 100 C18, 250×4 mm, 5 m

Mobile phase: MeOH/THF (1:1): $H_2O$=70:30

Flow rate: 0.8 ml min$^{-1}$

λ: 254 nm $t_R$: 14.7 min

Optical rotation: $[\alpha]_D^{20}$=−22.5 (c 0.8, DMSO).

$^1$H-NMR (500 MHz, DMSO-$d_6$, 75° C.): δ [ppm]=3.75-4.04 (m, 4H, 2×10-$H_a$, 2×2-$H_b$), 4.05-4.34 (m, 4H, 2×2-$H_b$, 2×1-H), 4.44 (t, J=10.0 Hz, 2H, 2×2-$H_a$), 6.93 (s, 1H, 3'-H), 7.40 (ddd, J=8.0, 7.0, 1.0 Hz, 2H, 7-H), 7.55 (ddd, J=8.0, 6.5, 1.0 Hz, 2H, 8-H), 7.69 (brs, 1H, 4-H), 7.84 (d, J=8.3 Hz, 2H, 2×9-H), 7.93 (s, 1H, 4-H), 8.12-8.39 (m, 4H, 6'-H, 8'-H, 2×6-H), 10.27 (s, 2H, 2×5-OH).

$^{13}$C-NMR (126 MHz, DMSO-$d_6$, 75° C.): δ [ppm]=40.8 (2×C-1), 47.8 (2×C-10), 55.8 (2×C-2), 95.4 (C-7'), 100.5 (2×C-4b), 116.1 (2×C-5a), 123.0 (2×C-9a), 123.3 (2×C-9), 123.7 (2×C-7), 123.8 (2×C-6), 125.1 (C-4a), 125.4 (C-3'), 127.9 (2×C-8), 130.6 (2×C-9a), 137.7 (C-6', C-8'), 139.6 (C-2', C-4'), 141.8, (2×C-3a), 154.8 (2×C-5), 166.0 (2×CON).

HRMS (ESI): m/z calculated for $C_{34}H_{25}Cl_2IN_2O_4$ 745.0134 [M+Na]+. found 745.0100.

5-((Trimethylsilyl)ethynyl)-1,3-phenylene)bis(((S)-1-(chloromethyl)-5-hydroxy-1,2-dihydro-3H-benzo[e]indol-3-yl)methanone) (55)

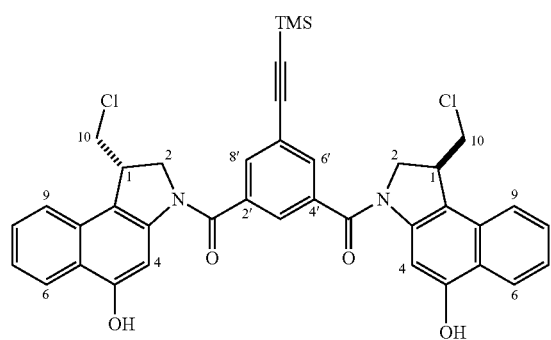

55

A solution of 54 (79 mg, 105 mol, 1.0 eq.) in triethylamine (420 µl) was admixed with tetrakis(triphenylphosphine)palladium(0) ((6 mg, 5 µmol, 5 mol %) and copper iodide (2 mg, 10 µmol, 10 mol %) and then ethynyl trimethylsilane (22 µl, 158 µmol, 1.5 eq.) was added at room temperature and the stirring was continued at the same temperature for 16 hours. Evaporation of the solvent under a high pressure gave the crude product, which was then purified by flash chromatography (EtOAc:PE 2:3 to EtOAc:PE 3:2) to give 55 (61 mg, 88%).

$R_f$: 0.4 (EtOAc:PE 1:1).

Optical rotation: $[\alpha]_D^{20}$=−43.8 (c 0.73, DMSO).

$^1$H-NMR (500 MHz, DMSO-$d_6$, 75° C.): δ [ppm]=3.82-3.93 (m, 2H, 2×10-$H_a$), 3.93-4.02 (m, 2H, 2×10-$H_b$), 4.02-4.23 (m, 4H, 2×2-$H_a$, 2×1-H), 4.44 (dd, J=11.2, 8.5 Hz, 2H, 2×2-$H_b$), 6.44 (s, 1H$_{minor}$, 3'-H) 6.93 (s, 1H, 3'-H), 7.40 (ddd, J=8.1, 6.8, 1.2 Hz, 2H, 2×7-H), 7.55 (ddd, J=8.2, 6.8, 1.4 Hz, 2H, 2×8-H), 7.69 (brs, 1H, 4-H), 7.80-8.02 (m, 5H, 4-H, 6'-H, 8'-H, 2×9-H), 8.17 (d, J=8.4 Hz, 2H, 2×6-H), 10.25 (s, 2H, 2×5-OH).

$^{13}$C-NMR (126 MHz, DMSO-$d_6$, 75° C.): δ [ppm]=0.3 (CH$_3$), 41.4 (2×C-1), 47.8 (2×C-10), 55.7 (2×C-2), 97.2 (Si—C≡), 100.5 (C-4), 104.2 (Ar-C≡), 116.1 (2×C-5a), 123.0 (2×C-9b), 123.3 (2×C-9), 123.7 (2×C-7), 123.8 (2×C-6), 124.0 (C-7'), 125.4 (C-3'), 126.0 (2×C-4), 127.9 (2×C-8), 130.6 (2×C-9a), 132.1 (C-6', C-8'), 138.5 (C-2', C-4'), 139.6 (2×C-3a), 141.8, 154.8 (2×C-5), 166.6 (2×CON).

HRMS (ESI): m/z calculated for $C_{39}H_{34}Cl_2N_2O_4Si$ 691.1587 [M–H]$^+$. found 691.1555.

5-Ethynyl-1,3-phenylene)bis(((S)-1-(chloromethyl)-5-hydroxy-1,2-dihydro-3H-benzo[e]indol-3-yl)methanone) (56)

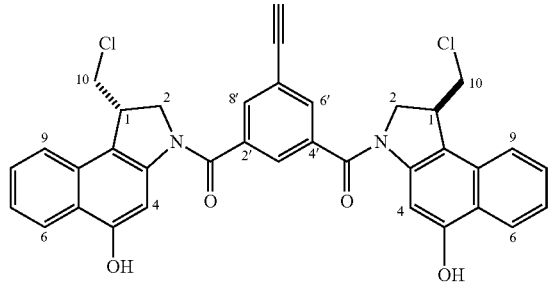

56

A stirred, precooled (0° C.) solution of 55 (61 mg, 881 µmol, 1.0 eq.) in THF (2 ml) was admixed with 70% hydrogen fluoride/pyridine (63 µl, 2.20 mmol, 25 eq.) and the stirring was continued at 35° C. for 12 hours. Additional 70% hydrogen fluoride/pyridine (63 µl, 2.20 mmol, 25 eq.) was added at 0° C. and the stirring was continued at 35° C. for a further 24 hours. The solvent was stripped off under a high pressure to give the crude product, which was then purified by flash chromatography (EtOAc:PE 2:3 to EtOAc:PE 1:1) to give 56 (39 mg, 71%). Starting material recovered (17 mg, 28%).

$R_f$: 0.3 (EtOAc:PE 1:1).

HPLC (analytical):

Column: Kromosil® 100 C18, 250×4 mm, 5 m

Mobile phase: MeOH/THF (1:1): $H_2O$=70:30

Flow rate: 0.8 mL min$^{-1}$

λ: 254 nm $t_R$: 11.0 min

Optical rotation: $[\alpha]_D^{20}$=−15.2 (c 0.46, DMSO).

$^1$H-NMR (500 MHz, DMSO-$d_6$, 75° C.): δ [ppm]=3.90 (dd, J=11.0, 7.4 Hz, 2H, 2×10-$H_a$), 3.98 (d, J=10.8 Hz, 2H, 2×10-$H_b$), 4.04-4.19 (m, 4H, 2×2-$H_a$, 2×1-H), 4.33 (s, 1H, CH), 4.44 (dd, J=11.1, 8.7 Hz, 2H, 2×2-$H_b$), 6.93 (s, 1H, 3'-H), 7.40 (ddd, J=8.2, 6.8, 1.1 Hz, 2H, 2×7-H), 7.55 (ddd, J=8.2, 6.8, 1.4 Hz, 2H, 2×8-H), 7.67 (s, 1H, 4-$H_a$), 7.84 (d, J=8.2 Hz, 2H, 2×9-H), 7.88-7.98 (m, 3H, 4-$H_b$, 6'-H, 8'-H), 8.18 (d, J=8.3 Hz, 2H, 2×6-H), 10.26 (s, 2H, 2×5-OH).

$^{13}$C-NMR (126 MHz, DMSO-$d_6$, 75° C.): δ [ppm]=41.4 (2×C-1), 47.8 (2×C-10), 55.8 (2×C-2), 82.7 (≡CH), 83.0 (Ar-C≡), 100.6 (C-4), 116.1 (2×C-5a), 123.0 (2×C-9b), 123.3 (2×C-9), 123.5 (C-7'), 123.7 (2×C-7), 123.8 (2×C-6), 125.4 (2×C-3'), 126.2 (C-4), 127.9 (2×C-8), 130.6 (2×C-9a), 132.2 (C-6', C-8'), 138.5 (C-2', C-4'), 139.6 (2×C-3a), 154.9 (2×C-5), 166.6 (2×CON).

HRMS (ESI): m/z calculated for $C_{36}H_{26}Cl_2N_2O_4$ 621.1348 [M+H]$^+$. found 621.1324.

(2R,3S,4S,5R,6S)-2-(Acetoxymethyl)-6-(((S)-1-(chloromethyl)-3-(3-((S)-1-(chloromethyl)-5-(((2R, 3S,4R,5R,6S)-3,4,5-triacetoxy-6-(acetoxymethyl) tetrahydro-2H-pyran-2-yl)oxy)-2,3-dihydro-1H-benzo[e]indole-3-carbonyl)-5-nitrobenzoyl)-2,3-dihydro-1H-benzo[e]indol-5-yl)oxy)tetrahydro-2H-pyran-3,4,5-triyl triacetate (LT-SH016) (57)

57

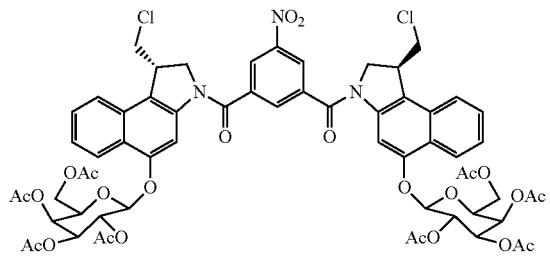

A solution of tbutoxycarbonylseco-CBI (0.336 mmol, 223 mg) in dry $CH_2Cl_2$ (20 ml) under an argon atmosphere was admixed with molecular sieve (4 Å) and O-(2,3,4,6-tetra-O-acetyl-/3-d-galactopyranosyl) trichloroacetimidate (170 mg, 0.344 mmol, 1.05 eq.). The solution was cooled to 0° C. and a solution of boron trifluoride-diethyletherate (0.504 mmol, 62 μl) in dry $CH_2Cl_2$ (2 ml) was added with stirring. The reaction mixture warmed up to room temperature and was stirred for a further 4 hours. The mixture was subsequently filtered and the filtrate was concentrated under reduced pressure. 5-Nitroisophthaloyl dichloride acyl chloride (0.168 mmol, 42 mg) and dry DMF (4 ml) were added to the crude material under an argon atmosphere. The mixture obtained was cooled to 00° C. and pyridine (1.344 mmol, 109 μl) was cautiously added. The reaction mixture warmed slowly to room temperature and was stirred overnight. After the end, the mixture was concentrated under reduced pressure and purified by flash chromatography ((PET/EtOAc, 1:0 to 1:1) to give the dimer 57 as an orange solid (0.066 mmol, 86 mg), 39% yield.

$R_f$ 0.25 (PET/EtOAc, 6:4)

Mp 172° C.

Optical rotation [α]$_D^{20}$=

IR (film): ν [$cm^{-1}$]=

UV ($CH_3CN$): $λ_{max}$ (lg ε)=

$^1$H-NMR (600 MHz, DMSO-$d_6$, 75° C.): δ 8.60 (d, J=1.5 Hz, 2H), 8.38 (s, 1H), 8.18 (br s, 2H), 8.03 (d, J=8.5 Hz, 2H), 7.95 (d, J=8.4 Hz, 2H), 7.61 (m, 2H), 7.49 (m, 2H), 5.56 (d, J=7.5 Hz, 2H), 5.49-5.40 (m, 6H), 4.57-4.47 (m, 4H), 4.22 (m, 2H), 4.19-4.04 (m, 6H), 4.02-3.97 (m, 2H), 3.94 (dd, J=11.0, 7.4 Hz, 2H), 2.19 (s, 6H), 2.04 (s, 6H), 2.01 (s, 6H), 1.98 (s, 6H).

$^{13}$C-NMR (126 MHz, DMSO-$d_6$, 75° C.): δ 169.30, 169.24, 168.83, 168.70, 164.53, 152.57, 147.86, 140.44, 138.18, 130.38, 129.15, 127.36, 124.21, 123.13, 122.67, 122.62, 121.72, 119.48, 101.88, 98.93, 70.47, 69.67, 68.48, 67.10, 61.01, 55.02, 46.71, 40.82, 20.06, 19.91, 19.90, 19.85.

HRMS (ESI) m/z calculated for $C_{62}H_{61}Cl_2N_3NaO_{24}$ [M+Na]$^+$: 1324.2914. found 1324.2909

(2R,3S,4S,5R,6S)-2-(Acetoxymethyl)-6-(((S)-3-(3-amino-5-((S)-1-(chloromethyl)-5-(((2R,3S,4R,5R, 6S)-3,4,5-triacetoxy-6-(acetoxymethyl)tetrahydro-2H-pyran-2-yl)oxy)-2,3-dihydro-1H-benzo[e]indole-3-carbonyl)benzoyl)-1-(chloromethyl)-2,3-dihydro-1H-benzo[e]indol-5-yl)oxy)tetrahydro-2H-pyran-3,4,5-triyl triacetate (LT-SH025) (58)

58

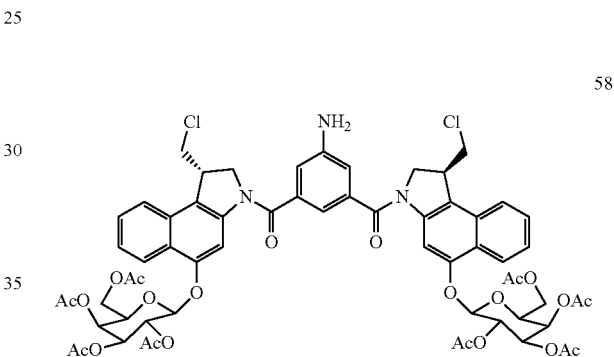

The dimer 57 (0.037 mmol, 48 mg) was dissolved in a mixture of MeOH/EtOAc (7:3, 5 ml) and conveyed twice over an H-Cube system (Pd/C 10%, full $H_2$ mode, 1 ml/min, room temperature). The mixture obtained was concentrated under reduced pressure and flash chromatography was carried out ($CH_2Cl_2$/MeOH, 98:2) to give the amine 58 as a white solid (0.034 mmol, 43 mg) with a yield of 92%.

$R_f$ 0.17 ($CH_2Cl_2$/MeOH, 96:4)

Mp 96° C.

$^1$H-NMR (600 MHz, DMSO-$d_6$, 75° C.): δ 8.00 (d, J=8.4 Hz, 2H), 8.00 (br s, 2H), 7.91 (d, J=8.4 Hz, 2H), 7.58 (m, 2H), 7.45 (m, 2H), 6.95 (m, 3H), 5.59-5.48 (m, 4H), 5.48-5.36 (m, 6H), 4.49 (m, 2H), 4.42 (dd, J=11.0, 9.2 Hz, 2H), 4.21-4.07 (m, 8H), 4.00 (dd, J=11.0, 2.8 Hz, 2H), 3.89 (dd, J=11.0, 7.1 Hz, 2H), 2.18 (s, 6H), 2.02 (s, 6H), 2.01 (s, 6H), 1.98 (s, 6H).

$^{13}$C-NMR (126 MHz, DMSO-$d_6$, 75° C.): δ 169.55, 169.47, 169.06, 168.94, 167.65, 152.63, 149.06, 140.98, 137.42, 129.37, 127.38, 124.03, 122.65, 122.40, 121.78, 119.17, 113.42, 111.50, 101.95, 98.97, 70.43, 69.73, 68.45, 67.11, 60.98, 55.00, 46.89, 40.42, 20.05, 19.94, 19.92, 19.86.

HRMS (ESI) m/z calculated for $C_{62}H_{64}Cl_2N_3O_{22}$ [M+H]$^+$: 1272.3353. found 1272.3349 and m/z calculated for $C_{62}H_{63}Cl_2N_3NaO_{22}$ [M+Na]$^+$: 1294.3172, found 1294.3169

(3-Amino-5-((S)-1-(chloromethyl)-5-(((2R,3S,4R,5S,6S)-3,4,5-trihydroxy-6-(hydroxymethyl)tetrahydro-2H-pyran-2-yl)oxy)-2,3-dihydro-1H-benzo[e]indole-3-carbonyl)phenyl)((S)-1-(chloromethyl)-5-(((2S,3R,4S,5R,6R)-3,4,5-trihydroxy-6-(hydroxymethyl)tetrahydro-2H-pyran-2-yl)oxy)-1,2-dihydro-3H-benzo 1[e]indol-3-yl)methanone (59) (LT-SH032)

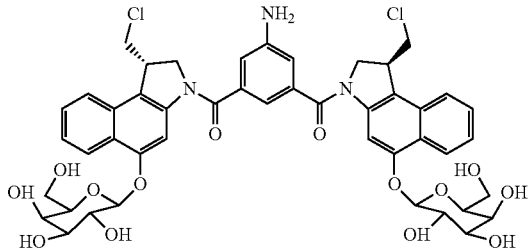

59

Aniline 58 (0.024 mmol, 31 mg) was taken up in MeOH (10 mil), and NaOMe (5.4 M in MeOH, 18 μl) was added at 0° C. with stirring. The reaction mixture warmed up to room temperature and was stirred for a further two hours. The mixture was subsequently diluted with $H_2O$ (1 mil) and neutralized (pH 7) by dropwise addition of 0.1 M aqueous HCl at 0° C. The mixture obtained was concentrated under reduced pressure and the residue was taken up with DMF (1.4 ml) and purified via preparative HPLC to give the above-stated compound as a white solid (0.0160 mmol, 15 mg) with a 66% yield.

HPLC analytical (Kromasil 100 C18, 250×4.0 mm, 5 μm)
$H_2O$/MeOH
0.8 ml/min
0-65 min 40:60 to 0:100
65-72 min 0:100
72-72 min 0:100 to 40:60
72-90 min 40:60
λ: 254 nm
$t_R$: 30.5 min
HPLC preparative (Kromasil 100 C18, 50×20 mm, 5 μm+Kromasil 100 C18, 250×20 mm, 7 μm)
$H_2O$/MeOH
16 ml/min
0-75 min 40:60 to 0:100
75-82 min 0:100
82-83 min 0:100 to 40:60
83-100 min 40:60
λ: 254 nm
$t_R$: 31.5 min
$^1$H-NMR (600 MHz, DMSO-$d_6$, 75° C.): δ 8.33 (d, J=8.1 Hz, 2H), 7.86 (d, J=8.4 Hz, 2H), 7.86 (br s, 2H), 7.55 (ddd, J=8.3, 6.8, 1.3 Hz, 2H), 7.41 (ddd, J=8.2, 6.8, 1.1 Hz, 2H), 6.98-6.93 (m, 3H), 5.50 (s, 2H), 5.05 (d, J=5.3 Hz, 2H), 4.89 (d, J=7.3 Hz, 2H), 4.58 (d, J=5.8 Hz, 2H), 4.40 (dd, J=11.1, 8.9 Hz, 2H), 4.37-4.30 (m, 4H), 4.18-4.09 (m, 4H), 3.99 (dd, J=11.1, 2.5 Hz, 2H), 3.88 (dd, J=11.1, 7.3 Hz, 2H), 3.84 (t, J=3.8 Hz, 2H), 3.79 (ddd, J=9.4, 7.7, 5.3 Hz, 2H), 3.69-3.62 (m, 2H), 3.61-3.55 (m, 4H), 3.55-3.49 (m, 2H),
$^{13}$C-NMR (126 MHz, DMSO-$d_6$, 75° C.): δ 167.66, 153.60, 149.02, 141.03, 137.52, 129.41, 127.16, 123.42, 123.13, 122.87, 122.34, 118.00, 113.53, 111.79, 102.09, 101.52, 75.04, 73.10, 70.41, 67.64, 59.73, 54.88, 46.97, 40.42.

HRMS (ESI) m/z calculated for $C_{46}H_{47}Cl_2KN_3O_{14}$ $[M+K]^+$: 974.2067. found 974.2059

FIGS. 8 to 14 set out the in vitro cytotoxicity of the above-stated synthesized compounds in human bronchial carcinoma cells of line A549. Clearly apparent is the activity of the example compounds; the IC50 values are shown correspondingly.

The invention claimed is:

1. A compound of the formula A-L-B, where A and B independently of one another are formed from

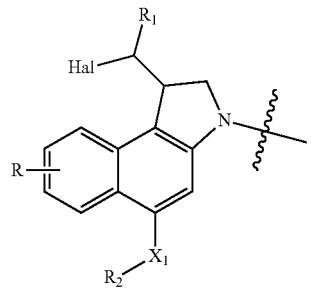

in which Hal is a halide selected from F, Cl, Br, and I;
R is H;
$R_1$ is H or a $C_1$-$C_4$ alkyl group;
$X_1$ is O, S, $NR_5$, where $R_5$ is selected from H and $C_1$-$C_4$ alkyl;
$R_2$ is hydrogen;
L is a linker for the covalent linkage of A and B, where L has the formula Z-Y-Z';
where Z and Z' independently of one another are selected from C=O, OC=O, and where Y represents:

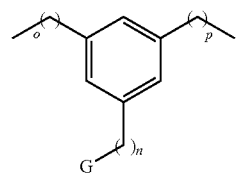

where n is 0 or 1;
o and p independently of one another are selected from an integer from 0 to 5;
where o and p may adopt the same value or a different value;
G is hydrogen or selected from the group consisting of an alkyne group, an amino group, a hydroxyl group, or a thiol group,
with the proviso that when n is 0, G is not hydrogen,
and pharmaceutically acceptable salts or pharmaceutically acceptable solvates thereof.

2. A compound as claimed in claim 1, where o and p independently of one another are an integral uneven number selected from the group consisting of 1, 3, and 5; and
Z and Z' are C=O.

3. A compound as claimed in claim 1, where Hal is Cl and $R_1$ is H.

4. A compound as claimed in claim 1, where L is a compound of formula II,

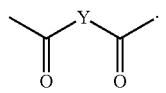
5. A pharmaceutical composition comprising a compound as claimed in claim 1.
6. The compound of claim 1 wherein n is zero and G is selected from the group consisting of an alkyne group, an amino group, a hydroxyl group, a thiol group.
* * * * *